US012716899B2

(12) United States Patent
Chackerian

(10) Patent No.: US 12,716,899 B2
(45) **Date of Patent: *Aug. 25, 2026**

(54) METHODS FOR DETERMINING DIFFERENCES IN ALPHA-4 INTEGRIN ACTIVITY BY CORRELATING DIFFERENCES IN sVCAM AND/OR sMAdCAM LEVELS

(71) Applicant: Biogen MA Inc., Cambridge, MA (US)

(72) Inventor: Alissa A. Chackerian, Sunnyvale, CA (US)

(73) Assignee: Biogen MA Inc., Cambridge, MA (US)

( * ) Notice: Subject to any disclaimer, the term of this patent is extended or adjusted under 35 U.S.C. 154(b) by 943 days.

This patent is subject to a terminal disclaimer.

(21) Appl. No.: 17/393,267

(22) Filed: Aug. 3, 2021

(65) Prior Publication Data

US 2022/0206012 A1 Jun. 30, 2022

Related U.S. Application Data

(62) Division of application No. 15/131,804, filed on Apr. 18, 2016, now Pat. No. 11,079,393, which is a division of application No. 13/881,520, filed as application No. PCT/US2011/057519 on Oct. 24, 2011, now abandoned.

(60) Provisional application No. 61/406,365, filed on Oct. 25, 2010, provisional application No. 61/406,358, filed on Oct. 25, 2010.

(51) Int. Cl.

| | |
|---|---|
| ***G01N 33/68*** | (2006.01) |
| ***C07K 16/28*** | (2006.01) |
| ***G01N 33/566*** | (2006.01) |
| *A61K 39/00* | (2006.01) |

(52) U.S. Cl.
CPC ..... *G01N 33/6893* (2013.01); *C07K 16/2839* (2013.01); *G01N 33/566* (2013.01); *A61K 2039/505* (2013.01); *C07K 2317/76* (2013.01); *G01N 2333/70503* (2013.01); *G01N 2333/70546* (2013.01); *G01N 2333/7056* (2013.01); *G01N 2500/00* (2013.01); *G01N 2800/52* (2013.01)

(58) Field of Classification Search
None
See application file for complete search history.

(56) References Cited

U.S. PATENT DOCUMENTS

2010/0317589 A1* 12/2010 Gelder .................... A61P 25/28 514/17.9

OTHER PUBLICATIONS

Millonig et al (Journal of Neuroimmunology, 227(1-2), Oct. 8, 2010, pp. 190-194, Available online Aug. 2010).*
Oppermann et al (Multiple Sclerosis, (Sep. 2009) vol. 15, No. 9, S, p. S133. Abstract No. P459).*

* cited by examiner

*Primary Examiner* — Brad Duffy
(74) *Attorney, Agent, or Firm* — Todd Lorenz

(57) ABSTRACT

Provided herein is a method of monitoring the change of the alpha-4 integrin activities in an individual by correlating with the soluble vascular cell adhesion molecule (sVCAM) and/or soluble mucosal addressin cell adhesion molecule (sMAdCAM) levels. Particularly, this method can be used, for example, to evaluate the pharmacokinetics and pharmacodynamics (PK/PD) of an alpha-4 integrin inhibitor used to treat a disease associated with pathological or chronic inflammation.

18 Claims, 19 Drawing Sheets

FIG. 1A

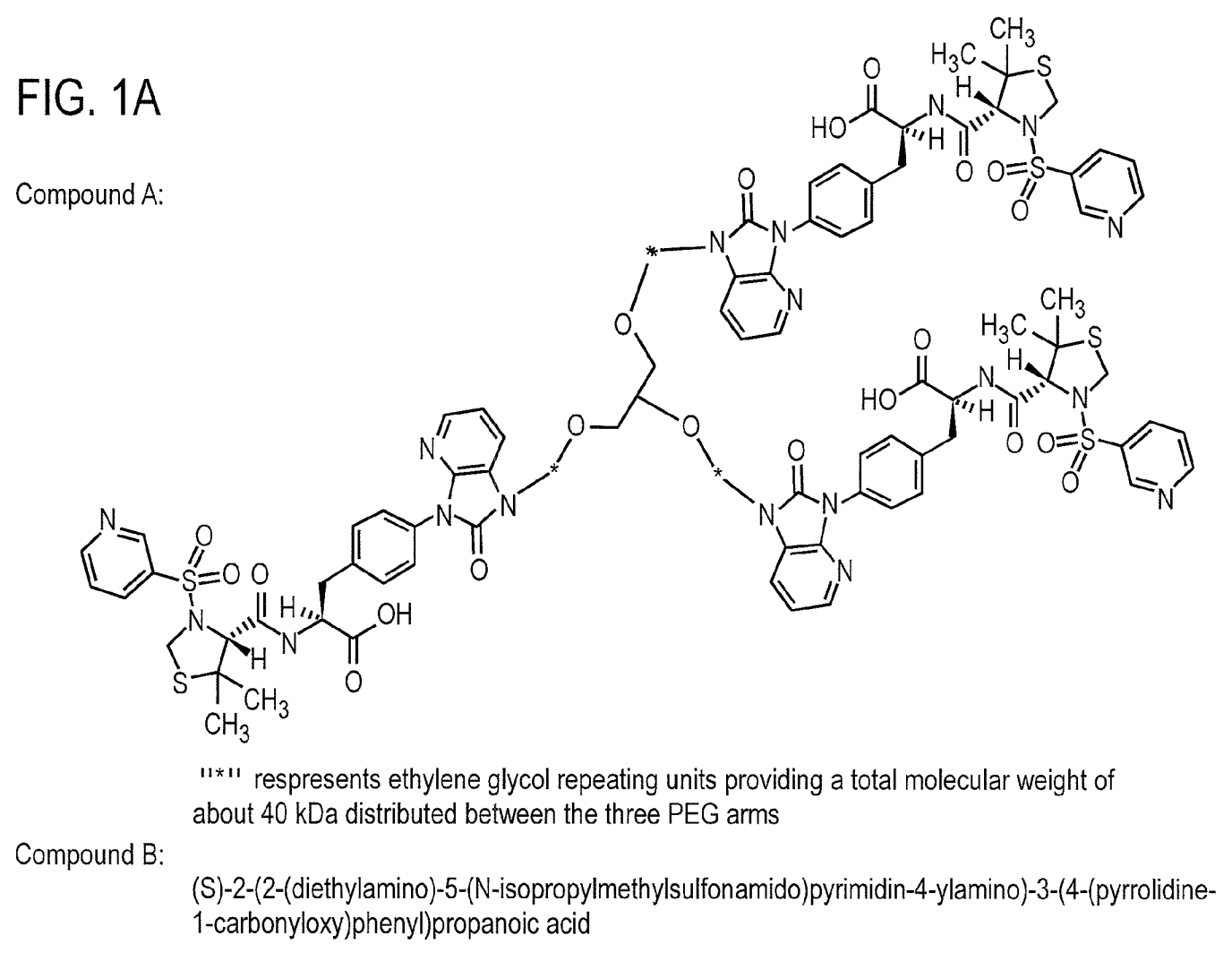

Compound A:

"*" respresents ethylene glycol repeating units providing a total molecular weight of about 40 kDa distributed between the three PEG arms Compound B:

(S)-2-(2-(diethylamino)-5-(N-isopropylmethylsulfonamido)pyrimidin-4-ylamino)-3-(4-(pyrrolidine-1-carbonyloxy)phenyl)propanoic acid

FIG. 1B

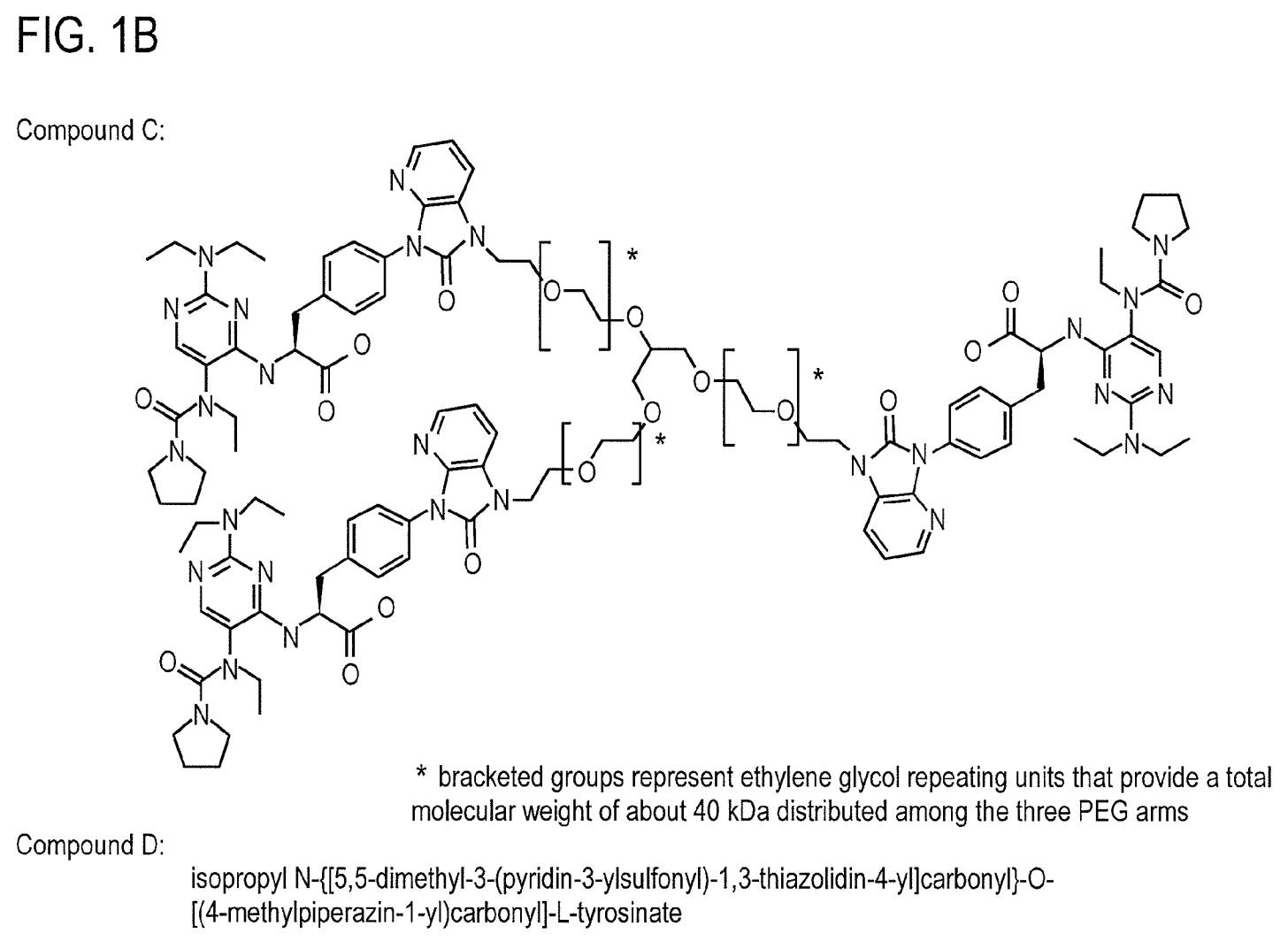

Compound C:

* bracketed groups represent ethylene glycol repeating units that provide a total molecular weight of about 40 kDa distributed among the three PEG arms Compound D:

isopropyl N-{[5,5-dimethyl-3-(pyridin-3-ylsulfonyl)-1,3-thiazolidin-4-yl]carbonyl}-O-[(4-methylpiperazin-1-yl)carbonyl]-L-tyrosinate

FIG. 2A

Experimental Autoimmune Encephalomyelitis

FIG. 2B

TNBS colitis

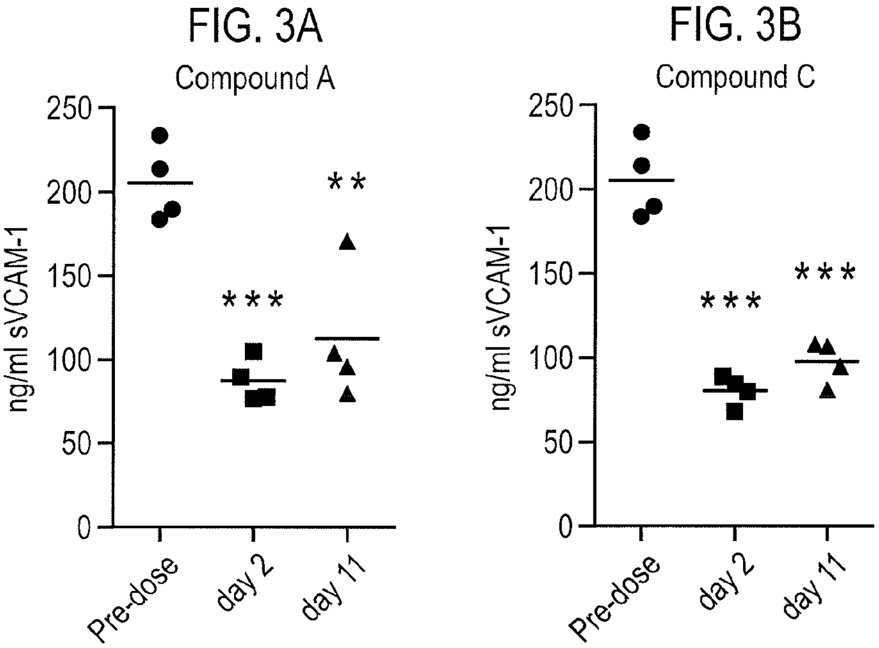
FIG. 3A
Compound A
250
200
150
100
50
0
ng/ml sVCAM-1
***
**
Pre-dose
day 2
day 11
FIG. 3B
Compound C
250
200
150
100
50
0
ng/ml sVCAM-1
***
***
Pre-dose
day 2
day 11
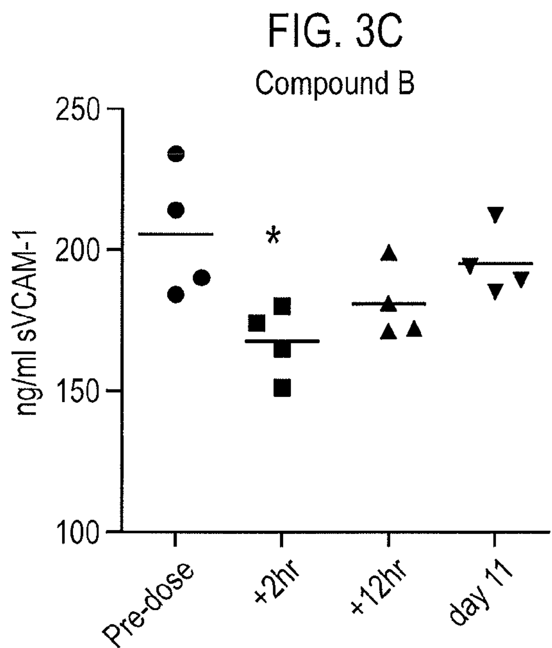
FIG. 3C
Compound B
250
200
150
100
ng/ml sVCAM-1
*
Pre-dose
+2hr
+12hr
day 11

α4 integrin expression on blood leukocytes geometric mean fluorescence - CD49d 600
550
500
450
400
350

***
***
*** vehicle
0.1 mg/kg Compound A
1 mg/kg Compound A
10 mg/kg Compound A sVCAM in plasma
1000
800
600
400
200
0
sVCAM (ng/ml)
***
***
vehicle
Compound A
PEG
Compound D Blood lymphocytes
20
15
10
5
0
Lymphocyte counts
(x10³/μl blood)
***
**
vehicle
Compound A
PEG
Compound D CD45RBhi transfer colitis
sMadCAM (pg/ml)
12000
6000
4000
2000
0
***
***
Naive SCID + vehicle
CD45RBhi transfer + Vehicle
CD45RBhi transfer + Compound C DSS induced colitis (chronic)
sMadCAM (pg/ml)
6000
4000
3000
2000
1000
0
*
***
Naive
DSS + Vehicle
DSS + Compound C DSS induced colitis (acute)
pg/ml sMAdCAM
2500
2000
1500
1000
500
0
BQL
BQL
DSS + vehicle
DSS + PS/2
DSS + Compound C in vitro selectivity of
Compound A and Compound C % Receptor Occupancy
120
100
80
60
40
20
0
0.001
0.01
0.1
1
10
100
1000
Compound concentration (nM)
α4β1 ($EC_{50}$ = 0.06 nM)
α4β7 ($EC_{50}$ = 6.62 nM)
Compound A
α4β1 ($EC_{50}$ = 0.16 nM)
α4β7 ($EC_{50}$ = 0.23 nM)
Compound B Receptor Expression
Normalized Expression (%)
100
75
50
25
0
α4β7
α4β1
0
7
14
21
Time (day)

Receptor Saturation
Receptor Saturation (%)
125
100
75
50
25
0
α4β1
α4β7
0
7
14
Time (day)

sVCAM vs. sMadCAM
% Baseline levels
100
75
50
25
0
sVCAM
sMadCAM
0
7
14
21
28
Time (day)

METHODS FOR DETERMINING DIFFERENCES IN ALPHA-4 INTEGRIN ACTIVITY BY CORRELATING DIFFERENCES IN sVCAM AND/OR sMAdCAM LEVELS

This application is a divisional of U.S. application Ser. No. 15/131,804, filed Apr. 18, 2016, which is a divisional of U.S. application Ser. No. 13/881,520, filed Sep. 4, 2013, which is a national stage application filed under 35 USC § 371 of PCT Application No. PCT/US2011/057519 filed Oct. 24, 2011, which claims the benefit of priority under 35 USC § 119(e) of provisional application Nos. 61/406,358, filed on Oct. 25, 2010, and 61/406,365, filed on Oct. 25, 2010, each of which are hereby incorporated by reference in its entirety.

FIELD

Described herein is a method of monitoring a change in alpha-4 integrin activity in an individual by correlating the activity with the level of a soluble molecule, wherein the soluble molecule is vascular cell adhesion molecule (sVCAM) and/or soluble mucosal addressin cell adhesion molecule (sMAdCAM).

BACKGROUND

The inflammatory response of vascularized tissues to infection or injury is affected by adhesion of leukocytes to the endothelial cells of blood vessels and their infiltration into the surrounding tissues. In a normal inflammatory response, the infiltrating leukocytes release toxic mediators, phagocytize debris and dead cells, and play a role in tissue repair and the immune response. However, in pathological inflammation, infiltrating leukocytes are over-responsive and can cause serious or fatal damage. Integrins belong to a family of cell-surface glycoproteins involved in cell-adhesion, immune cell migration, and activation. Alpha-4 integrin is expressed by circulating leukocytes and forms heterodimeric receptors in conjunction with either the beta-1 or the beta-7 integrin subunit. Both alpha-4 beta-1 ($\alpha 4\beta 1$, or very late antigen-4 (VLA-4)) and alpha-4 beta-7 ($\alpha 4\beta 7$) dimers play a role in the migration of leukocytes across the vascular endothelium and contribute to cell activation and survival within the parenchyma.

The alpha-4 beta-1 dimer binds to vascular cell adhesion molecule-1 (VCAM-1), which is expressed by the vascular endothelium at many sites of chronic inflammation. The alpha-4 beta-7 dimer interacts with mucosal addressin cell adhesion molecule (MAdCAM-1), and mediates homing of lymphocytes to the gut.

Adhesion molecules such as alpha-4 integrins are potential targets for treating pathological and chronic inflammation. Alpha-4 integrin inhibitors have been tested for their anti-inflammatory potential both in vitro and in vivo in animal models. The in vitro experiments demonstrate that alpha-4 integrin inhibitors block attachment of lymphocytes to activated endothelial cells. Experiments testing the effect of alpha-4 integrin inhibitors in animal models having an artificially induced condition simulating multiple sclerosis (MS), experimental autoimmune encephalomyelitis (EAE), have demonstrated that anti-alpha-4 integrin inhibitors prevent brain inflammation and subsequent paralysis in the animals. Similarly, alpha-4 integrin inhibitors have been shown to protect against intestinal inflammation in animal models of inflammatory bowel disease (IBD). Collectively, these experiments identify alpha-4 integrin inhibitors as potentially useful therapeutic agents for diseases associated with pathological and chronic inflammation, such as MS and IBD.

However, there has been no efficient and reliable method to study the pharmacokinetics and pharmacodynamics of agents that inhibit alpha-4 integrin. The currently available methods typically involve (1) measuring receptor saturation and receptor down-modulation in fresh blood samples by flow cytometry, or (2) enumerating lymphocytes in freshly harvested blood samples. Both methods rely on the same-day analysis of fresh samples, which can be inconvenient when analyzing clinical samples. Additionally, these methods are not considered to be very sensitive measures of the functional inhibition of alpha-4 integrins. Recently, Millonig et al., *J. Neuroimmunol.* 227: 190-194 (2010) observed a statistically significant decrease of soluble VCAM-1 (sVCAM) in MS patients 4 weeks after administering Natalizumab. Natalizumab is a humanized monoclonal antibody that specifically binds the $\alpha$-chain of alpha-4 integrins. Millonig et al. suggested that the sVCAM level reached a steady state level of inhibition four weeks after the first Natalizumab application. Although Millonig et al. speculated that sVCAM might be a treatment efficacy monitoring tool, Millonig et al. admitted that both the clinical usefulness of the observed correlation and its biological significance remain to be elucidated.

Accordingly, there remains a need in the field to develop more efficient and accurate methods, e.g., identifying and employing a reliable biomarker, to evaluate the pharmacokinetics and pharmacodynamics of $\alpha 4$ integrin inhibitors, which can be applied to treat various inflammatory and autoimmune diseases.

SUMMARY

The inhibition of alpha-4 integrin activity, whether by antibodies or small molecules, correlates with a decrease in sVCAM and/or sMAdCAM level in bodily fluids. The decrease of sVCAM and/or sMAdCAM levels is dose-dependent and can be observed within days or even hours. Furthermore, the correlation between the inhibition of alpha-4 integrin and the decreased levels of sVCAM and/or sMAdCAM is seen in healthy individuals, as well as diseased individuals, thus is independent of the disease state. Accordingly, sVCAM and/or sMAdCAM can be used as a pharmacodynamic biomarker for the biological activity of an agent such as an antibody or drug that modulates alpha-4 integrin activity. Pharmacodynamic and pharmacokinetic parameters of alpha-4 integrin modulators thus can be determined with respect to the in vivo biological activity of the modulator, without potential interference by inactive modulator metabolites, for example. Better characterization of these parameters will permit more accurate alpha-4 integrin modulator dosing regimens, for example, which can minimize potentially harmful side effects.

Accordingly, an in vitro method of determining a difference in alpha-4 integrin activity in an individual is provided comprising: a) measuring a soluble molecule in a first biological sample obtained from the individual immediately before administration of an alpha-4 integrin inhibitor; b) measuring the soluble molecule in a second biological sample, wherein the second biological sample has been obtained from the individual within thirty-one (31) days after administration of the alpha-4 integrin inhibitor; and c) determining whether there is a decrease in the levels of the soluble molecule between the first and second biological samples, wherein the decrease correlates with a decrease in alpha-4 integrin activity in the individual, and thereby determining whether there is a difference in alpha-4 integrin activity in the individual after administration of the alpha-4 integrin inhibitor compared with before administration of the alpha-4 integrin inhibitor, and wherein the soluble molecule is sVCAM and/or sMAdCAM. The second biological sample may be obtained, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days after the individual is treated with the alpha-4 integrin inhibitor.

The method may further comprise detecting a decrease in the levels of the soluble molecule in the second biological sample compared with the first biological sample, and attributing said decrease to a decrease in alpha-4 integrin activity in the individual after administration of the alpha-4 integrin inhibitor compared with before administration of the alpha-4 integrin inhibitor. Additionally, the method may further comprise determining whether an adjustment in treatment of the individual is required, wherein no decrease or a statistically insignificant decrease ($p>0.05$) in the levels of the soluble molecule between the first and second biological samples indicates ineffective response to the alpha-4 integrin inhibitor requiring a treatment adjustment of the individual.

Optionally, the method may further comprise detecting no decrease, or detecting a statistically insignificant decrease ($p>0.05$), in the level of the soluble molecule in the second biological sample compared with the first biological sample, and concluding that a treatment adjustment of the individual is required. The treatment adjustment may comprise changing to a different alpha-4 integrin inhibitor or increasing the dosage of the alpha-4 integrin inhibitor.

In one aspect, alpha-4 integrin activity may be alpha-4 beta-1 integrin activity, and the soluble molecule is sVCAM. In another aspect, alpha-4 integrin activity is alpha-4 beta-7 integrin activity, and wherein the soluble molecule is sMAdCAM.

In yet another aspect, the individual who has the administration of the alpha-4 integrin inhibitor has a disease or disorder associated with a pathological or chronic inflammation. The disease or disorder may be selected from the group consisting of multiple sclerosis (MS), meningitis, encephalitis, inflammatory bowel disease, rheumatoid arthritis (RA), asthma, acute juvenile onset diabetes, AIDS dementia, atherosclerosis, nephritis, retinitis, atopic dermatitis, psoriasis, myocardial ischemia, chronic prostatitis, complications from sickle cell anemia, lupus erythematosus, and acute leukocyte-mediated lung injury. The alpha-4 integrin inhibitor is an antibody or a small molecule.

In a further aspect, the first and/or the second biological sample is selected from the group consisting of a tissue, a cell, and a body fluid. The first and/or the second biological sample may be in the form of frozen plasma or serum. A body fluid may be selected from the group consisting of blood, lymph, sera, plasma, urine, semen, synovial fluid, saliva, tears, bronchoalveolar lavage, and cerebrospinal fluid. The soluble molecule in the biological samples may be measured by a method selected from the group consisting of enzyme-linked immunosorbent assays (ELISA), radioimmunoassay (RIA), Western blotting, and microbead-based protein detection assay.

Also provided is an in vitro use of sVCAM and/or sMAdCAM as a pharmacodynamic biomarker for the activity of (i) alpha-4 integrin or (ii) a modulator of alpha-4 integrin activity. The alpha-4 integrin activity may be alpha-4 beta-1 integrin activity, and the pharmacodynamic biomarker may be sVCAM. The alpha-4 integrin activity may be alpha-4 beta-7 integrin activity, and the pharmacodynamic biomarker may be sMAdCAM. The modulator of alpha-4 integrin activity may be an alpha-4 integrin inhibitor, for example, an antibody or a small molecule. The in vitro use of sVCAM and/or sMAdCAM as a pharmacodynamic biomarker for the activity may be useful in an individual receiving treatment with a modulator of alpha-4 integrin activity. The individual may have a disease or disorder associated with a pathological or chronic inflammation. The disease or disorder associated with a pathological or chronic inflammation may be selected from the group consisting of multiple sclerosis (MS), meningitis, encephalitis, inflammatory bowel disease, rheumatoid arthritis (RA), asthma, acute juvenile onset diabetes, AIDS dementia, atherosclerosis, nephritis, retinitis, atopic dermatitis, psoriasis, myocardial ischemia, chronic prostatitis, complications from sickle cell anemia, lupus erythematosus, and acute leukocyte-mediated lung injury.

BRIEF DESCRIPTION OF THE DRAWINGS

The accompanying drawings are incorporated into the specification and provide non-limiting illustration of various embodiments. In the drawings:

FIG. 1A-1B depicts exemplary alpha-4 integrin inhibitors (Compounds A-D) used in the Examples.

Figures 2A, 2B:
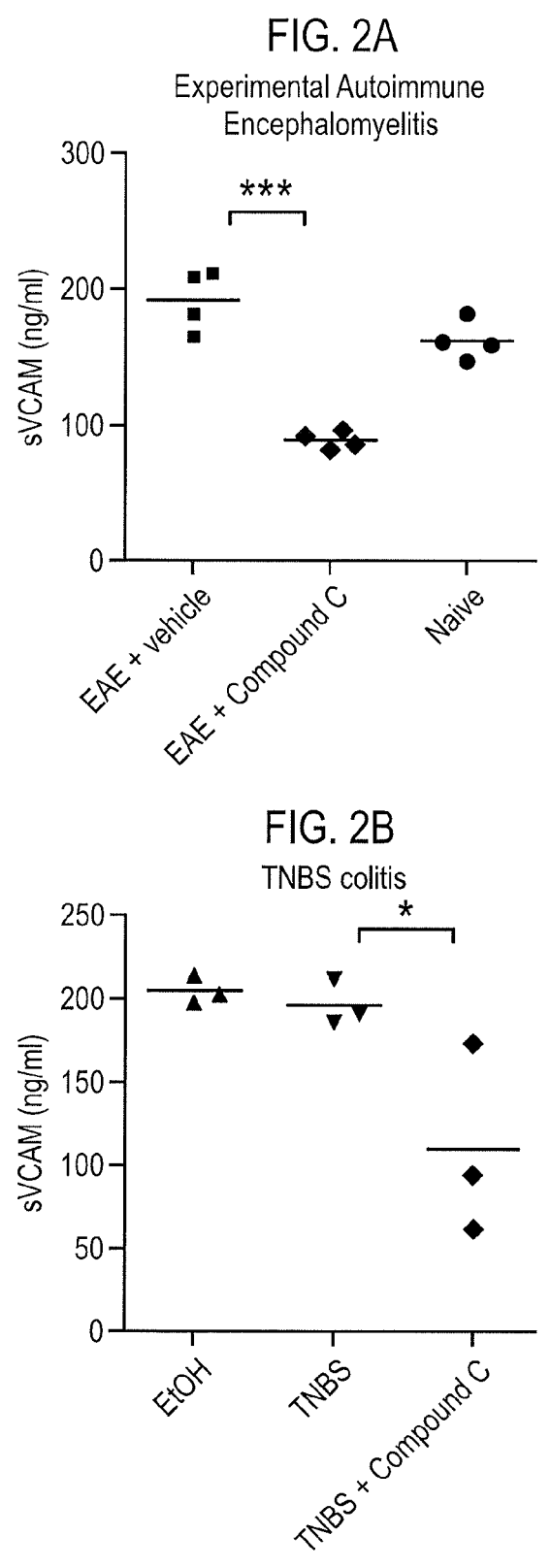

FIG. 2A-2D depicts decreased levels of sVCAM in various rat disease models treated with small molecule alpha-4 integrin inhibitors. Experiments were performed as described in Example 1.

FIG. 3A-C depicts decreased levels of sVCAM in normal rats treated with small molecule alpha-4 integrin inhibitors. Experiments were performed as described in Example 2.

FIG. 5A-5F depicts that the effect of alpha-4 integrin inhibitors on sVCAM down-regulation is dose-dependent and correlates with other markers of alpha-4 integrin inhibition. Experiments were performed as described in Example 4.

DETAILED DESCRIPTION

1. Definitions

Figure 2C:
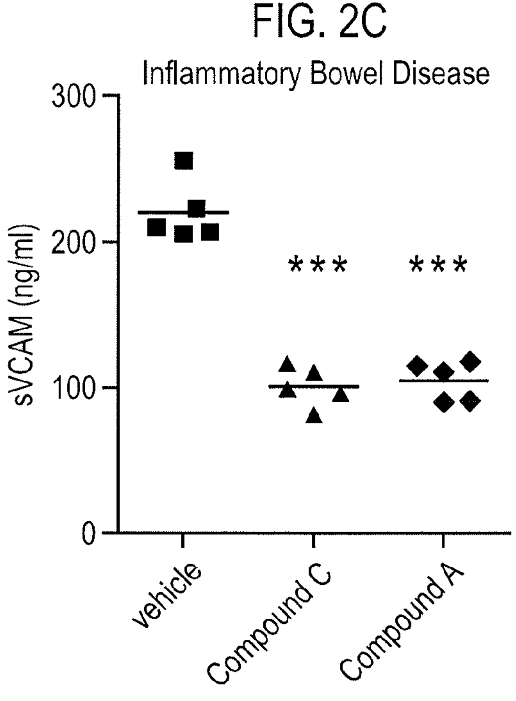

An "individual" as used herein may be any of mammalian animals (e.g., domesticated animals), including human, dog, cat, cattle, horse, goat, pig, swine, sheep, monkey, rat, and mouse. In one embodiment, the individual can be a human.

The term "pathological and chronic inflammation" as used herein refers to an inappropriate inflammation associated with disorders including, but not limited to, asthma, atherosclerosis, AIDS dementia, diabetes, inflammatory bowel disease, rheumatoid arthritis, transplant rejection, graft versus host disease, multiple sclerosis (especially in MS involving further demyelination), for example, primary progressive multiple sclerosis (PPMS), secondary progressive multiple sclerosis (SPMS), relapsing-remitting multiple sclerosis (RRMS), and progressive relapsing multiple sclerosis (PRMS), tumor metastasis, nephritis, atopic dermatitis, psoriasis, myocardial ischemia, chronic prostatitis, complications from sickle cell anemia, lupus erythematosus, and acute leukocyte mediated lung injury. Such inflammation is characterized by a heightened response of inflammatory cells, including infiltrating leukocytes. Over time, such pathological inflammation often results in damage to tissue in the region of inappropriate inflammation.

The term "alpha-4 integrin activity" as used herein refers to the accessible amount of alpha-4 integrins, including both the alpha-4 beta-1 and alpha-4 beta-7 dimers, presented on the leukocyte cell surface. Alpha-4 integrin activity can be determined using any technique known in the art. For example, alpha-4 integrin activity can be evaluated directly through cytometry using a fluorescently-labeled antibody specific to alpha-4 integrins. See, e.g., U.S. Pat. No. 7,807,167. Alternatively, alpha-4 integrin activity can be evaluated indirectly by measuring leukocyte infiltration in tissue samples. See, e.g., U.S. Pat. No. 7,435,802; see also Krumbholz et al., *Neurology* 71: 1350-1354 (2008).

The term "biological sample" as used herein refers to a biological material from an individual. A biological sample may be, as non-limiting examples, a tissue, cell, whole blood, serum, body fluids, plasmic fluid, autoptical tissue sample (e.g., brain, skin, lymph node, spinal cord), cultured cells or supernatants from cultured cells. The biological sample used will vary based on the assay format, the detection method, and the nature of the sample to be assayed. Methods for preparing biological samples are well known in the art and can be readily adapted in order to obtain a biological sample that is compatible with the method utilized.

The term "body fluid" used herein includes fluids that are found in individuals. They include fluids that are excreted or secreted from the body, as well as fluids that normally are not excreted or secreted. These fluids include, as non-limiting examples, aqueous humor, blood, serum, interstitial fluid, lymph, mucus, pleural fluid, saliva, plasma, urine, semen, tears, synovial fluid, wound fluid, and/or cerebrospinal fluid. Typically, blood including blood serum and blood plasma are used in the present embodiments.

The terms "specifically binds" or "binds specifically" as used herein means that one member of a specific binding pair will not show any statistically significant binding to molecules other than its specific binding partner. A binding partner may show at least 1000 times the affinity of binding (measured as an apparent association constant) for its specific binding pair partner than a non-specific binding partner. For example, antibodies that bind to an alpha-4 integrin with a binding affinity of $10^7$ mole/L or more, typically $10^8$ mole/1 or more, are said to bind specifically to an alpha-4 integrin.

The term "diagnostic kit" as used herein includes typically a detection system with different packages of diagnostic antibodies and/or reagents that are necessary for the quantitative and/or qualitative evaluation of a biomarker. Kits generally include instructions for using the reagents and/or diagnostic antibodies. The antibodies, as well as any reagent, can be provided as a liquid, powder, tablet, or suspension. The antibodies and/or reagents may be provided in separate packages suitable for application separately.

Unless defined otherwise, all technical and scientific terms used herein have the same meaning as commonly understood by one of ordinary skill in the art. It must be noted that as used herein, the singular forms "a", "and", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

2. Alpha-4 Integrin Inhibitors

Various types of alpha-4 integrin inhibitors having the ability to bind to and inhibit alpha-4 integrin activity can be used in the present embodiments. Many such inhibitors have been identified and characterized, and representative examples are described below. Given the teachings disclosed herein, it is well within the skill of one in the art to identify other alpha-4 integrin inhibitors that will be able to inhibit the alpha-4-comprising integrin dimers in a manner that biologically mimics or is similar to the specifically described inhibitors. The present embodiments also include the chronic administration of such inhibitors and combinations thereof.

2.1. Antibodies or Immunologically Active Fragments

In one embodiment, the alpha-4 integrin inhibitors are antibodies or immunologically active fragments thereof that selectively bind to an alpha-4 integrin or a dimer comprising alpha-4, such as alpha-4 beta-1 or alpha-4 beta-7. Representative alpha-4 integrin antibodies are known in the art, including for example (1) Natalizumab, disclosed in U.S.

Pat. Nos. 5,168,062, 5,385,839, 5,730,978, 5,840,299, 6,033,665, and 6,602,503, (2) the CD49d antibodies manufactured by Biolegend (San Diego, CA); and (3) PS/2 which is a rat anti-mouse alpha-4 integrin antibody (the PS/2 hybridoma is available from the ATCC (Rockville, MD)). Non-limiting example of alpha-4 integrin antibodies include those disclosed in U.S. Pat. Nos. 5,565,332, 5,733,743, 5,837,242, 5,858,657, 5,871,734, 5,871,907, 5,872,215, 5,885,793, 5,888,507, 5,932,214, 5,969,108, 6,140,471, 6,172,197, 6,180,336, 6,225,447, and 7,176,184.

In one embodiment, the alpha-4 integrin inhibitor can be a monoclonal antibody. In another embodiment, the antibody may be chemically modified, e.g., by pegylation. Additionally, other antibodies can be identified using techniques available in the art. For example, antibodies capable of specifically binding to alpha-4 integrin can be produced using phage display technology. Antibody fragments that selectively bind to an alpha-4 integrin or a dimer comprising an alpha-4 integrin can then be isolated. Exemplary methods for producing such antibodies via phage display are disclosed in U.S. Pat. No. 6,225,447, for example.

Monoclonal antibodies can also be produced using the conventional hybridoma methods. These methods have been widely applied to produce hybrid cell lines that secrete high levels of monoclonal antibodies against many specific antigens, and can also be used to produce monoclonal antibodies capable of specifically binding to alpha-4 integrins. For example, mice (e.g., Balb/c mice) can be immunized with an antigenic alpha-4 integrin epitope by intraperitoneal injection. After sufficient time has passed to allow for an immune response, the mice are sacrificed, and the spleen cells obtained and fused with myeloma cells, using techniques well known in the art. The resulting fused cells, hybridomas, are then grown in a selective medium, and the surviving cells grown in such medium using limiting dilution conditions. After cloning and recloning, hybridomas can be isolated for secreting antibodies (for example, of the IgG or IgM class or IgG1 subclass) that selectively bind to the target, alpha-4 integrin or a dimer comprising an alpha-4 integrin. To produce agents specific for human use, the isolated monoclonal can then be used to produce chimeric and humanized antibodies.

Antibodies that can be used as alpha-integrin inhibitors include, but are not limited to, polyclonal, monoclonal, multispecific, human, humanized or chimeric antibodies, single chain antibodies (e.g., scFv), Fab fragments, F(ab') fragments, fragments produced by a Fab expression library, anti-idiotypic (anti-Id) antibodies (including, e.g., anti-Id antibodies to antibodies of the present embodiments), and epitope-binding fragments of any of the above. Typically, the antibodies are human antigen-binding antibody fragments, which include, but are not limited to, Fab, Fab' and $F(ab')_2$, Fd, single-chain Fvs (scFv), single-chain antibodies, disulfide-linked Fvs (sdFv), and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included are antigen-binding fragments that can comprise any combination of variable region(s) with a hinge region, CH1, CH2, and CH3 domains. The antibodies may be from any animal origin including birds and mammals. Typically, the antibodies are human, murine (e.g., mouse and rat), donkey, sheep, monkey, rabbit, goat, guinea pig, pig, camel, horse, or chicken (or other avian). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example in, U.S. Pat. No. 5,939,598.

Chimeric and humanized antibodies can be produced from non-human antibodies, and can have the same or similar binding affinity as the antibody from which they are produced. Techniques for producing chimeric antibodies (Morrison et al., 1984 *Proc. Nat'l. Acad. Sci*. USA 81: 6851; Neuberger et al., 1984 *Nature* 312: 604; Takeda et al., 1985 *Nature* 314: 452) include splicing the genes from, e.g., a mouse antibody molecule of appropriate antigen specificity together with genes from a human antibody molecule of appropriate biological activity. For example, a nucleic acid encoding a variable (V) region of a mouse monoclonal antibody can be joined to a nucleic acid encoding a human constant (C) region, e.g., IgG1 or IgG4. The resulting antibody is thus a species hybrid, generally with the antigen binding domain from the non-human antibody and the C or effector domain from a human or primate antibody.

Humanized antibodies are antibodies with variable regions that are primarily from a human antibody (i.e., the acceptor antibody), but which have complementarity determining regions substantially from a non-human antibody (the donor antibody). See, e.g., Queen et al., *Proc. Nat'l. Acad. Sci USA* 86: 10029-10033 (1989); WO 90/07861, U.S. Pat. Nos. 7,435,802, 6,054,297; 5,693,761; 5,585,089; 5,530,101; and 5,224,539. The constant region or regions of these antibodies are generally also from a human antibody. The human variable domains are typically chosen from human antibodies having sequences displaying a high homology with the desired non-human variable region binding domains. The heavy and light chain variable residues can be derived from the same antibody, or a different human antibody. In addition, the sequences can be chosen as a consensus of several human antibodies, such as described in WO 92/22653.

A "Primatized™ antibody" is a recombinant antibody containing primate variable sequences or antigen binding portions, and human constant domain sequences. See, e.g., Newman, *Bio/Technology,* 1992, 10: 1455-60. Primatization of antibodies results in the generation of antibodies that contain monkey variable domains and human constant sequences. See, e.g., U.S. Pat. No. 6,113,898. This technique modifies antibodies such that they are not rejected upon administration in humans because they are antigenic. This technique relies on immunization of cynomolgus monkeys with human antigens or receptors. This technique was developed to create high affinity monoclonal antibodies directed to human cell surface antigens.

Specific amino acids within the human variable region are selected for substitution based on the predicted conformation and antigen binding properties. This can be determined using techniques such as computer modeling, prediction of the behavior and binding properties of amino acids at certain locations within the variable region, and observation of effects of substitution. For example, when an amino acid differs between a non-human variable region and a human variable region, the human variable region can be altered to reflect the amino acid composition of the non-human variable region. In a specific embodiment, the antibodies used in the chronic dosage regime are humanized antibodies as disclosed in U.S. Pat. No. 5,840,299. In another embodiment, transgenic mice containing human antibody genes can be immunized with an antigenic alpha-4 integrin structure and hybridoma technology can be used to generate human antibodies that selectively bind to alpha-4 integrin.

Chimeric, human, primatized, and/or humanized antibodies can be produced by using recombinant expression, e.g., expression in human hybridomas (Cole et al., Monoclonal Antibodies and Cancer Therapy, Alan R. Liss, p. 77 (1985)), in myeloma cells, or in Chinese hamster ovary (CHO) cells. Alternatively, antibody coding sequences can be incorporated into transgenes for introduction into the genome of a transgenic animal and subsequent expression in the milk of the transgenic animal. See, e.g., U.S. Pat. No. 6,197,946. Suitable transgenes include transgenes having a promoter and/or enhancer from a mammary gland specific gene, for example casein or β-lactoglobulin.

2.2. Small Molecules

Small molecules for use in the present embodiments may encompass compounds having a molecular weight of more than 50 and less than about 4,000 Daltons. Alternatively, these compounds may have covalently attached polyethylene glycol polymer chains (i.e., pegylation) to improve various properties of the compounds, for example, extended half-life, improved tissue penetration, and improved solubility. The pegylated conjugates thus may have a molecular weight about 40 kilodaltons (kDa). Alpha-4 integrin inhibitors comprise functional groups necessary for structural interaction with proteins, particularly hydrogen bonding, and may include an amine, carbonyl, hydroxyl, or carboxyl group, typically at least two of functional chemical groups. The alpha-4 integrin inhibitors often comprise cyclical carbon or heterocyclic structures and/or aromatic or polyaromatic structures substituted with one or more of the above-described functional groups. Alpha-4 integrin inhibitors may include, but not limited to: peptides, saccharides, fatty acids, steroids, purines, pyrimidines, derivatives, structural analogs, or combinations thereof. Non-limiting examples of alpha-4 integrin inhibitors are described, for example, in U.S. Pat. No. 5,998,447 (heterocycles), 6,034,238 (heterocyclic compounds), 6,331,552 (substituted imidazolidine), 6,399,643 (spiroimidazolidine derivatives), 6,423,712 (2,4-substituted imidazolidine derivatives), 6,514,952 (hydantoin derivatives), 6,521,654 (substituted imidazolidine derivatives), 6,667,331 (non-peptidyl compounds), 6,667,334 (imidazolidine derivatives), 6,668,527 (non-peptidyl compounds), 6,680,333 (imidazolidine derivatives), 6,756,378, 6,759,424 (imidazolidine derivatives), 6,838,439 (heterocytes), 6,903,128 (non-peptidyl compounds), 6,962,937 (imidazolidine derivatives), 7,179,819, and 7,196,112. Several representative small molecule alpha-4 integrin inhibitors are shown in FIG. 1.

2.3. Anti-Alpha-4 Integrin Peptides

The present embodiments also include any peptide that is capable of binding to an alpha-4 integrin or a dimer comprising an alpha-4 subunit. Included are peptides that are substantially homologous to a region of the extracellular matrix or a natural ligand of the specific alpha-4 integrin receptor or receptors targeted. For example, for the chronic inhibition of alpha-4 beta-1 receptor, peptides can be used that comprise at least a portion of the fibronectin IIICS region (e.g., peptides comprising at least a portion of the CS-1 peptide sequence or a sequence substantially homologous to the CS-1 sequence) can be used to bind to a receptor and inhibit the activity of the alpha-4 comprising integrin. See, e.g., U.S. Pat. No. 7,238,668.

3. Use of Alpha-4 Integrin Inhibitors to Treat Diseases Associated with Pathological or Chronic Inflammation Alpha-4 integrin inhibitors can be used to treat various diseases associated with pathological or chronic inflammation by blocking alpha-4-dependent interactions. The alpha-4-dependent interaction with the VCAM-1 ligand on endothelial cells is an early event in many inflammatory responses, including those of the central nervous system. Undesired diseases and conditions resulting from inflammation and having acute and/or chronic clinical exacerbations include multiple sclerosis (Yednock et al., 1992 *Nature* 356: 63; Baron et al., 1993 *J. Exp. Med.* 177: 57), meningitis, encephalitis, stroke, other cerebral traumas, inflammatory bowel disease (IBD) including ulcerative colitis and Crohn's disease (CD) (Hamann et al., 1994 *J. Immunol.* 152: 3238; Podolsky et al., 1993 *J. Clin. Invest.* 92: 372), rheumatoid arthritis (van Dinther-Janssen et al., 1991 *J. Immunol.* 147: 4207; van Dinther-Janssen et al., 1993 *Annals Rheumatic Diseases* 52: 672; Elices et al., 1994 *J. Clin. Invest.* 93: 405; Postigo et al., 1992 *J. Clin. Invest.* 89: 1445), asthma (Mulligan et al., 1993 *J. Immunol.* 150: 2407) and acute juvenile onset diabetes (Type 1) (Yang et al., 1993 *Proc. Nat'l Acad. Sci. USA* 90: 10494; Burkly et al., 1994 Diabetes 43: 529; Baron et al., 1994 *J. Clin. Invest.* 93: 1700), AIDS induced dementia (Sasseville et al., 1994 *Am. J. Path.* 144: 27); atherosclerosis (Cybulsky et al., 1991 *Science* 251: 788-91, Li et al., 1993 *Arterioscler. Thromb.* 13: 197), nephritis (Rabb et al., 1995 *Springer Semin. Immunopathol.* 16: 417-25), retinitis, atopic dermatitis, psoriasis, myocardial ischemia, chronic prostatitis, complications from sickle cell anemia, lupus erythematosus, and acute leukocyte-mediated lung injury such as occurs in adult respiratory distress syndrome.

Inflammatory bowel disease is a collective term for two similar diseases referred to as Crohn's disease (CD) and ulcerative colitis. CD is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrienes, prostaglandin, and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles, and knees. The arthritis results from interaction of synovial cells with leukocytes that infiltrate from the circulation into the synovial lining of joints. See, e.g., Paul, Immunology 3rd ed., Raven Press, 1993.

Alpha-4 integrin inhibitors can be used in the treatment of organ or graft rejection. Over recent years, there has been a considerable improvement in the efficiency of surgical techniques for transplanting tissues and organs such as skin, kidney, liver, heart, lung, pancreas, and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. CD8+ cells, CD4+ cells, and monocytes are all involved in the rejection of transplant tissues. Antibodies directed to alpha-4 integrin are useful, inter alia, to block alloantigen-induced immune responses in the donee thereby preventing such cells from participating in the destruction of the transplanted tissue or organ. See, e.g., Paul et al., 1996 Transplant International 9: 420-425; Georczynski et al., 1996 *Immunol.* 87: 573-580); Georcyznski et al., 1995 *Transplant. Immunol.* 3: 55-61; Yang et al., 1995 *Transplantation* 60: 71-76; and Anderson et al., 1994 *APMIS* 102: 23-27. A related use for the alpha-4 integrin inhibitors is modulating the immune response involved in "graft versus host" disease (GVHD). See, e.g., Schlegel et al., *J. Immunol.* 155: 3856-3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia, and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. Alpha-4 integrin inhibitors are used, inter alia, to block activation of the donor T-cells thereby interfering with their ability to lyse target cells in the host.

Alpha-4 integrin inhibitors may be useful in inhibiting tumor metastasis. Several tumor cells have been reported to express alpha-4 integrin and antibodies to alpha-4 integrin have been reported to block adhesion of such cells to endothelial cells. See, e.g., Steinback et al., 1995 *Urol. Res.* 23: 175-83; Orosz et al., 1995 *Int. J. Cancer* 60: 867-71; Freedman et al., 1994 *Leuk Lymphoma* 13: 47-52; and Okahara et al., 1994 *Cancer Res.* 54: 3233-6.

Alpha-4 integrin inhibitors may be useful in treating multiple sclerosis. Multiple sclerosis (MS) is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against alpha-4 beta-1 integrin have been shown to block the adhesion of leukocytes to the endothelium, and thus prevent inflammation of the central nervous system and subsequent paralysis in the animals. The onset of MS may be dramatic or so mild as to not cause a patient to seek medical attention. The most common symptoms include weakness in one or more limbs, visual blurring due to optic neuritis, sensory disturbances, diplopia, and ataxia. The course of disease may be stratified into three general categories: (1) relapsing MS, (2) chronic progressive MS, and (3) inactive MS. Relapsing MS is characterized by recurrent attacks of neurologic dysfunction. MS attacks generally evolve over days to weeks and may be followed by complete, partial or no recovery. Recovery from attacks generally occurs within weeks to several months from the peak of symptoms, although rarely some recovery may continue for 2 or more years. Chronic progressive MS results in gradually progressive worsening without periods of stabilization or remission. This form develops in patients with a prior history of relapsing MS, although in 20% of patients, no relapses can be recalled. Acute relapses also may occur during the progressive course. A third form is inactive MS. Inactive MS is characterized by fixed neurologic deficits of variable magnitude. Most patients with inactive MS have an earlier history of relapsing MS. The course of MS is also dependent on the age of the patient. For example, favorable prognostic factors include early onset (excluding childhood), a relapsing course and little residual disability 5 years after onset. By contrast, poor prognosis is associated with a late age of onset (i.e., age 40 or older) and a progressive course. These variables are interdependent, since chronic progressive MS tends to begin at a later age that relapsing MS. Disability from chronic progressive MS is usually due to progressive paraplegia or quadriplegia in individual patients.

Alpha-4 integrin inhibitors may be used with effective amounts of other therapeutic agents against acute and chronic inflammation. Such agents include other antagonists of adhesion molecules (e.g., other integrins, selectins, and immunoglobulin (Ig) super family members). See, e.g., Springer, 1990 *Nature* 346: 425-433; Osborn, 1990 Cell 62: 3; Hynes, 1992 *Cell* 9: 11. Other anti-inflammatory agents that can be used in combination with the alpha-4 integrin inhibitors include antibodies and other antagonists of cytokines, such as interleukins IL-1 through IL-13, tumor necrosis factors $\alpha$ and $\beta$, interferons $\alpha$, $\beta$, and $\gamma$, tumor growth factor beta (TGF-$\beta$), colony stimulating factor (CSF) and granulocyte monocyte colony stimulating factor (GM-CSF). Other anti-inflammatory agents may also include antibodies and other antagonists of chemokines such as MCP-1, MIP-1$\alpha$, MIP-1$\beta$, RANTES, exotaxin, and IL-8. Other anti-inflammatory agents may further include NSAIDS, steroids, and other small molecule inhibitors of inflammation.

4. Use of Alpha-4 Integrin Inhibitors to Treat Autoimmune Diseases

Alpha-4 integrin inhibitors also can be used to treat various autoimmune diseases. An autoimmune disease herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and autoimmune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, diabetic retinopathy, diabetic nephropathy, diabetic large-artery disorder, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (*Anemia perniciosa*), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjögren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, lymphoid interstitial pneumonitis (LIP), bronchiolitis obliterans (non-transplant) vs NSIP, Guillain-Barré syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia areata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, filariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, tyrosinosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis.

5. Use of Alpha-4 Integrin Inhibitors to Treat Cancer

Alpha-4 integrin inhibitors also can be used to treat cancer. See, e.g., U.S. Published Patent Application No. 20090312353. The term cancer embraces a collection of malignancies with each cancer of each organ consisting of numerous subsets. Typically, at the time of cancer diagnosis, "the cancer" consists in fact of multiple subpopulations of cells with diverse genetic, biochemical, immunologic, and biologic characteristics.

The types of cancers to be treated by an alpha-4 integrin inhibitor can be those that exhibit alpha-4 integrins or their ligands (for example, ligands of alpha-4 integrins include VCAM-1 and/or MAdCAM-1). Representative cancers include, but are not limited to, hematological malignancies, acute lymphoblastic leukemia (ALL), acute myelogenous leukemia (AML), chronic myelogenous leukemia (CML), chronic lymphocytic leukemia (CLL), and multiple myeloma (MM). Leukemias may be lymphoblastic or myelogenous. Lymphoblastic (or lymphocytic) leukemia affects lymphocytes. Myelogenous leukemia affects myelocytes.

Lymphocytic neoplastic diseases may be characterized by a massive expansion of a single B-cell clone, detectable by measuring the excessively-produced antibodies, measured in a serum protein electrophoresis test or peripheral blood flow cytometry. Such an expansion is said to be "monoclonal," and monoclonal antibodies produced by such a group of B-cells can cause illnesses such as amyloidosis and lupus, or can be indicative of an underlying malignancy. The concept of clonality is closely associated with malignancy, for example in diagnosing lymphomatoid skin lesions. The expansion of a particular clone of immune B-cells is usually interpreted by clinicians as evidence of unrestricted cell growth, the hallmark of cancer. Lymphoid leukemia (or lymphocytic leukemia) is a type of leukemia affecting lymphoid tissue. These leukemias are commonly divided by the stage of maturation at which the clonal (neoplastic) lymphoid population stopped maturing (i.e., acute lymphoblastic leukemia or chronic lymphoblastic leukemia).

Acute lymphoblastic leukemia (ALL), also known as acute lymphocytic leukemia, is a form of leukemia of the white blood cells. Malignant, immature white blood cells continuously multiply and are overproduced in the bone marrow. As a result, normal cells are crowded out of the bone marrow, and metastasize to other organs. "Acute" refers to the undifferentiated, immature state of the circulating lymphocytes, and to the rapid progression of disease, which can be fatal in weeks to months if left untreated.

Chronic lymphoblastic leukemia (CLL; also known as chronic lymphoid leukemia), affects B cells. B cells normally originate in the bone marrow and develop in the lymph nodes. In CLL, the DNA of B cells are damaged, so the cells no longer fight infection. However, the B cells continue to grow and crowd out the healthy blood cells. Thus, CLL is characterized by an abnormal neoplastic proliferation of B cells.

Most people are diagnosed without symptoms as the result of a routine blood test that returns a high white blood cell count. However, as it advances, CLL causes swollen lymph nodes, spleen, and liver, and eventually anemia and infections. Early CLL is not treated, and late CLL is treated with chemotherapy and monoclonal antibodies. Survival varies from 5 years to more than 25 years.

Acute myelogenous leukemia (AML), also known as acute myeloid leukemia, is a cancer of the myeloid line of white blood cells, characterized by the rapid proliferation of abnormal cells which accumulate in the bone marrow and interfere with the production of normal blood cells. The symptoms of AML are caused by replacement of normal bone marrow with leukemic cells, resulting in a drop in red blood cells, platelets, and normal white blood cells. These symptoms include fatigue, shortness of breath, easy bruising and bleeding, and increased risk of infection. As an acute leukemia, AML progresses rapidly and is typically fatal within weeks or months if left untreated.

Acute myelogenous leukemia (AML) is a potentially curable disease; but generally only a minority of patients are cured with current therapy. AML can be treated initially with chemotherapy aimed at inducing a remission. Some patients may further receive a hematopoietic stem cell transplant.

Chronic myelogenous leukemia (CML) is a form of leukemia characterized by the increased and unregulated growth of predominantly myeloid cells in the bone marrow and the accumulation of these cells in the blood. CML is a clonal bone marrow stem cell disorder causing the proliferation of mature granulocytes (neutrophils, eosinophils, and basophils) and their precursors. Historically, it has been treated with chemotherapy, interferon and bone marrow transplantation.

Multiple myeloma (MM) is a malignant proliferation of plasma cells that typically originates in bone marrow and involves the skeleton. MM presents clinical features attributable to the particular sites of involvement and abnormalities in formation of plasma proteins. The condition is usually characterized by numerous diffuse foci or nodular accumulations of abnormal or malignant plasma cells in the marrow of various bones (especially the skull), causing palpable swellings of the bones, and occasionally in extraskeletal sites. Upon radiological exam, the bone lesions may have a characteristic "punched out" appearance.

The cells involved in the myeloma typically produce abnormal proteins and/or abnormal protein levels in the serum and urine. MM typically develops from monoclonal gammopathy of undetermined significance (MGUS) to smoldering multiple myeloma (SMM) to multiple myeloma (MM). Symptoms of these conditions may include hypercalcemia, renal insufficiency, fatigue, anemia, bone pain, spontaneous fractures, increased frequency or duration of infection, or abnormal urine color or odor. An "M-spike" refers to a monoclonal peak that is typically visualized as a narrow band on electrophoretic gel, or an abnormal arc in immunoelectrophoresis. It represents a proliferation of homogenous immunoglobulin produced by clone cells originating from a single common cell, e.g., a monoclonal immunoglobulin characterized by a heavy chain of a single class and subclass, and light chain of a single type (also referred to as M-protein, a monoclonal protein, and more broadly as a paraprotein).

6. VCAM-Mediated Diseases and Diseases Having Elevated sVCAM Levels

VCAM-mediated diseases include all diseases mediated by VCAM. See, e.g., WO 2010/053316. Non-limiting examples of VCAM-mediated diseases include cancers, allergic responses, atherosclerosis, cardiovascular diseases, HIV (human immunodeficiency virus, AIDS) disease, arthritis, pneumonia, hypercholesterolemia, sepsis, dermatitis, psoriasis, Crohn's disease, cystic fibrosis, post transplantation late and chronic solid organ rejection, cell or islet transplantation rejection, multiple sclerosis, systemic lupus erythematosis, Graves' disease, thrombotic disease, inflammatory bowel diseases, autoimmune diabetes, diabetic retinopathy, rhinitis, ischemia-reperfusion injury, post-angioplasty restenosis, osteomyelitis, cold, influenza virus disease, chronic obstructive pulmonary disease (COPD), glomerulonephritis, Graves disease, gastrointestinal allergies, sickle cell disease, and conjunctivitis.

Additionally, sVCAM levels elevated in various diseases and disorders. See, e.g., WO 2009/141786. Non-limiting examples of these diseases and disorders having elevated sVCAM levels include sickle cell disease (SCD), multiple myeloma, cardiovascular disease (atherosclerosis), myocardial infarction, colorectal cancer, Hodgkin's disease, coronary artery disease, atherosclerotic aortic or thoracic disease, breast cancer, Dengue virus infection, hemorrhagic fever, idiopathic pulmonary fibrosis, acute respiratory distress syndrome, renal function in patients with sickle cell disease (albuminuria), preeclampsia, eclampsia, allergic contact dermatitis, myeloma, non-Hodgkin's lymphoma, Hodgkin's lymphoma, ovarian cancer, renal cancer, bladder cancer, gastrointestinal cancer, proliferative vitreoretinopathy, diabetic retinopathy, endometriosis, systemic lupus erythematosus (SLE), acute myeloid leukemia, hypertriglyceridemia, heart transplant, pulmonary sarcoidosis, stroke, coronary artery disease, atherosclerosis, type II diabetes, cardiopulmonary bypass, sepsis, chronic renal failure, renal allograft, Graves' disease, deep vein thrombosis, and allergic rhino-conjunctivitis (allergic rhinitis).

7. MAdCAM as a Target to Treat Inflammatory Diseases

Mucosal addressin cell adhesion molecule (MAdCAM) is a member of the immunoglobulin superfamily of cell adhesion receptors. While MAdCAM plays a physiological role in gut immune surveillance, it appears to facilitate excessive lymphocyte extravasation in inflammatory bowel disease under conditions of chronic gastrointestinal tract inflammation. Antibodies that inhibit the binding of $\alpha4\beta7$-positive lymphocytes to MAdCAM have been shown to reduce lymphocyte recruitment, tissue extravasation, inflammation, and disease severity in animal models. Anti-MAdCAM antibodies or composition containing thereof have been suggested to be useful in treating various inflammatory diseases. See, e.g., U.S. Published Patent Application No. 2009/0238820. Non-limiting inflammatory diseases that may be treated with an anti-MAdCAM antibody include Crohn's disease, ulcerative colitis, diverticula disease, gastritis, liver disease, primary biliary sclerosis, sclerosing cholangitis, peritonitis, appendicitis, biliary tract disease, acute transverse myelitis, allergic dermatitis (e.g., allergic skin, allergic eczema, skin atopy, atopic eczema, atopic dermatitis, cutaneous inflammation, inflammatory eczema, inflammatory dermatitis, flea skin, military dermatitis, military eczema, house dust mite skin), ankylosing spondylitis (Reiters syndrome), asthma, airway inflammation, atherosclerosis, arteriosclerosis, biliary atresia, bladder inflammation, breast cancer, cardiovascular inflammation (e.g., vasculitis, rheumatoid nail-fold infarcts, leg ulcers, polymyositis, chronic vascular inflammation, pericarditis, chronic obstructive pulmonary disease), chronic pancreatitis, perineural inflammation, colitis (including amoebic colitis, infective colitis, bacterial colitis, Crohn's colitis, ischemic colitis, ulcerative colitis, idiopathic proctocolitis, inflammatory bowel disease, psuodomembranouscolitis), collagen vascular disorders (rheumatoid arthritis, systemic lupus erythematosus, progressive systemic sclerosis, mixed connective tissue disease, diabetes mellitus), Crohn's disease (regional enteritis, granulomatous ileitis, ileocolitis, digestive system inflammation), demyelinating disease (including myelitis, multiple sclerosis, disseminated sclerosis, acute disseminated encephalomyelitis, perivenous demyelination, vitamin B12 deficiency, Guillain-Barre syndrome, MS-associated retrovirus), dermatomyositis, diverticulitis, exudative diarrheas, gastritis, granulomatous hepatitis, granulomatous inflammation, cholecystitis, insulin-dependent diabetes mellitus, liver inflammatory diseases (liver fibrosis primary biliary cirrhosis, hepatitis, sclerosing cholangitis), lung inflammation (idiopathic pulmonary fibrosis, eosinophilic granuloma of the lung, pulmonary histiocytosis X, peribronchiolar inflammation, acute bronchitis), lymphogranuloma venereum, malignant melanoma, mouth/tooth disease (including gingivitis, periodontal disease), mucositis, musculoskeletal system inflammation (myositis), nonalcoholic steatohepatitis (nonalcoholic fatty liver disease), ocular & orbital inflammation (including uveitis, optic neuritis, peripheral rheumatoid ulceration, peripheral corneal inflammation), osteoarthritis, osteomyelitis, pharyngeal inflammation, polyarthritis, proctitis, psoriasis, radiation injury, sarcoidosis, sickle cell neuropathy, superficial thrombophlebitis, systemic inflammatory response syndrome, thuroiditis, systemic lupus erythematosus, graft versus host disease, acute burn injury, Behcet's syndrome, and Sjogrens syndrome.

8. Detection of sVCAM and/or sMAdCAM sVCAM and/or sMAdCAM can be detected in biological samples. See, e.g., Leung et al., *Immunol. Cell Biol.* 82:400-409 (2004). The biological sample can be typically body fluid from an individual, for example, blood, serum, semen, urine, cerebrospinal fluid, or saliva. In some embodiments, the fluid can be a cell-free sample; however the inclusion of cells in a body fluid sample does not preclude the detection and/or quantification of sVCAM and/or sMAdCAM. In particular examples, the fluid can be serum or plasma. sVCAM and/or sMAdCAM can be detected using a diagnostic kit, for example.

Many techniques employing immunological techniques are known for the detection and quantification of a protein or protein fragments. Examples of methods for the detection of protein antigens in biological samples, including methods employing dip strips or other immobilized assay devices, are disclosed, for instance in the following patents: U.S. Pat. No. 5,965,356 (Herpes simplex virus type seroassay); U.S. Pat. No. 6,114,179 (Method and test kit for detection of antigens and/or antibodies); and U.S. Pat. No. 6,057,097 (Marker for pathologies comprising an autoimmune reaction and/or inflammatory disease). These methods could readily be adapted for detection of sVCAM and/or sMAdCAM.

By way of example, Western blot analysis can be used to detect and quantify sVCAM and/or sMAdCAM in a body fluid sample. In a typical Western blot, proteins are electrophoretically separated on an acrylamide gel, then transferred to a membrane and detected with one or more antibodies. The antibody detection may be direct or indirect. For direct antibody visualization of the sVCAM or sMAdCAM protein, the blot membrane is incubated with a labeled, sVCAM or sMAdCAM-specific binding agent, for example a sVCAM or a sMAdCAM antibody conjugated to alkaline phosphatase or horseradish peroxidase. For indirect antibody visualization of the sVCAM or sMAdCAM protein, the blot membrane is incubated first with an unconjugated sVCAM-specific or sMAdCAM antibody (primary antibody), then with a labeled antibody (secondary antibody) that recognizes the primary antibody. For instance, secondary antibodies for the indirect detection of primary antibodies are often conjugated with a detectable moiety, such as horseradish peroxidase, alkaline phosphatase, or radioactive or fluorescent tags.

Alternatively, a sandwich ELISA assay can be used to detect and quantify the sVCAM and/or sMAdCAM. A typical sandwich ELISA format involves a specific immobilized capture antibody, sample, a labeled detection antibody, chromogens, and stop solution. Antigen will bind to the immobilized capture antibody and thus can be detected with one or more antibodies. The antibody detection technique used with an ELISA may be direct or indirect. For direct antibody visualization of the sVCAM or sMAdCAM protein, anti-sVCAM or anti-sMAdCAM antibody is attached to a substrate, the substrate is incubated with a body fluid sample, and the substrate is then incubated with another anti-sVCAM or anti-sMAdCAM antibody that has been enzyme-conjugated, for example, an anti-sVCAM antibody or anti-sMAdCAM antibody conjugated to alkaline phosphatase or horseradish peroxidase. For indirect antibody visualization of the sVCAM or sMAdCAM protein, an anti-sVCAM antibody or anti-sMAdCAM antibody is attached to the substrate, and the substrate is incubated with a body fluid sample. The substrate is then incubated with an unconjugated sVCAM-specific or sMAdCAM-specific antibody (primary antibody), then with an enzyme-conjugated antibody (secondary antibody) that recognizes the primary antibody. Secondary antibodies for the indirect detection of primary antibodies are often conjugated with horseradish peroxidase or alkaline phosphatase. A substrate solution is then added, acted upon by the enzyme, and effects a color change. The intensity of the color change is proportional to the amount of antigen in the original sample. Primary and secondary antibodies also can be coupled to radioactive or fluorescent tags. The intensity of radioactive or fluorescent labeling is proportional to the amount of antigen present in the original sample.

Optionally, a microbead-based protein detection assay (also called microsphere assay or flow-based bead assay) can be used to detect sVCAM and/or sMAdCAM in biological samples, such as a serum sample from an individual. This technology, as represented by systems developed by Luminex Corporation (Austin, TX) and other systems developed by Becton Dickinson (Franklin Lakes, NJ), allows one to process a very small amount of sample, typically 20 μl, to detect a protein, such as sVCAM and/or sMAdCAM. One aspect of this assay is based on the coupling of a capture antibody to microspheres containing specific amounts of, for instance, a red dye and an infrared dye. After incubation of the microspheres with the sample, a secondary detection antibody coupled with biotin and streptavidin coupled with phycoerythrin, the beads are analyzed with a flow cytometer or other flow-based fluorescence detection systems. One laser detects the beads and a second one detects the intensity of the phycoerythrin bound to those beads (technical notes are available from Luminex Corp., for instance at their website or through their catalog).

EXAMPLES

The following examples are provided in order to demonstrate and further illustrate certain representative embodiments and aspect of the present disclosure and are not to be construed as limiting the scope thereof.

Materials and Methods

Alpha-4 Integrin Inhibitors

Exemplary alpha-4 integrin inhibitors (Compounds A-D) are shown in FIG. 1.

Quantification of Plasma Concentration of Compound A

Compound A was measured using a LC/MS/MS method. Following the addition of an internal standard, plasma samples (anticoagulant: lithium heparin) were extracted using protein precipitation (acetonitrile with 0.1% formic acid). After evaporation of the filtered supernatant to dryness, and reconstitution, the extracts were analyzed by LC-API/MS/MS. The MRM (multiple reaction monitoring) transitions for Compound A and the IS were m/z 257/114 and 270/91, respectively. The lower limit of quantification was 20 ng/mL.

Blood Lymphocyte Count

Lymphocytes were quantified from whole blood samples collected in tubes containing the anti-coagulant EDTA via a Cell-Dyn 3700 hematology analyzer (Abbott Diagnostics).

Detection/Quantification of Alpha-4 Integrin Expression

Whole blood was collected into tubes containing the anti-coagulant lithium heparin. Samples were stained with AlexaFluor647-labeled anti-mouse CD49d (alpha-4 integrin) antibody (Biolegend, San Diego, CA) for 30 minutes. Red blood cells were lysed (FACS lysing solution, BD Biosciences, San Jose, CA) and samples were washed twice in PBS containing 5% fetal bovine serum. Stained cells were analyzed for shifts in the geometric mean fluorescence intensity using a BD FACScan flow cytometer.

Example 1—sVCAM is Down-Regulated During Alpha-4 Integrin Inhibition in Various Rat Disease Models (w/ Small Molecule Inhibitors)

Alpha-4 integrin inhibition resulted in sVCAM down-regulation in three models of inflammatory disease in rats. Compounds A and C are pegylated small-molecule inhibitors of alpha-4 integrin. Compound B is a non-pegylated small molecule inhibitor of alpha-4 integrin. All serum samples were analyzed by Rules Based Medicine, Inc (Austin, TX) with the RodentMAP assay, a multiplexed bead-based immunoassay on a Luminex instrument (Luminex Corporation, Austin, TX) to determine quantities of sVCAM in rat serum. Statistics were performed with one-way ANOVA.

The results are presented in FIG. 2. As shown in FIG. 2A, Lewis rats were intradermally injected with guinea pig spinal cord and brain white matter homogenate in complete Freund's adjuvant and treated subcutaneously with cyclosporine A (2 mg/kg every other day) for 20 days to induce chronic experimental autoimmune encephalomyelitis. On day 30 post-induction, rats were treated with vehicle (phosphate buffered saline, PBS) or 10 mg/kg Compound C every 3 days. On day 40 post-induction, serum samples were collected and analyzed for sVCAM content.

As shown in FIG. 2B, Sprague-Dawley rats were intrarectally instilled with 2,4,6-trinitrobenzene sulfonic acid (TNBS) to induce colitis or ethanol alone as a control. At days 1 and 4 post-TNBS instillation, rats were dosed subcutaneously with 10 mg/kg Compound C. On day 5, serum samples were collected and analyzed for sVCAM content.

Figure 2D:
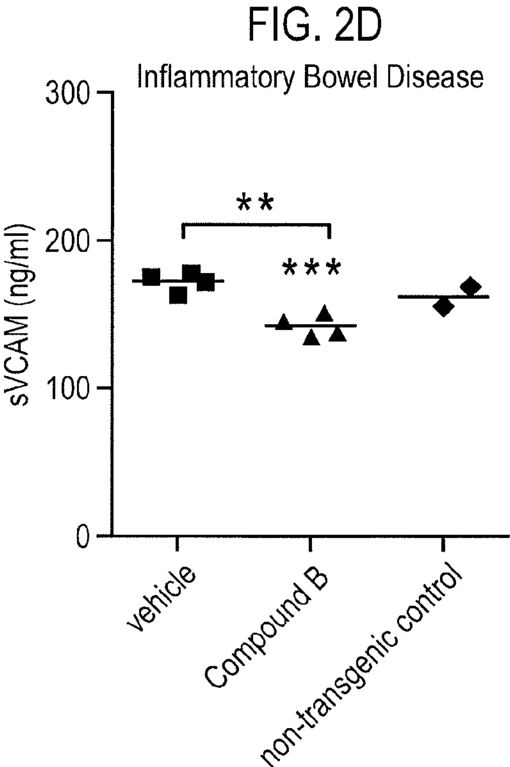

As shown in FIGS. 2C and 2D, rats carrying a human HLA.B27 transgene spontaneously develop symptoms of inflammatory bowel disease as they age. HLA.B27 transgenic rats were treated subcutaneously with Compound C (10 mg/kg every 3 days), Compound A (10 mg/kg every 5 days), Compound B (100 mg/kg twice a day), or vehicle (PBS) at 16-20 weeks of age. Serum was sampled after 20 (FIG. 2C) or 5 (FIG. 2D) days of treatment, and sVCAM levels were assessed. Alpha-4 integrin inhibition in each inflammatory disease model tested resulted in a statistically significant decrease in serum levels of sVCAM (*p<0.05; p<0.01; *p<0.001).

Example 2—Alpha-4 Integrin Inhibition Results in Reduced sVCAM in Normal Rats (w/ Small Molecule Inhibitors)

In order to test whether alpha-4 integrin inhibition regulates sVCAM levels in the absence of disease, normal (i.e., non-diseased) rats were injected with alpha-4 inhibitors, and sVCAM levels were measured. Sprague Dawley rats were injected subcutaneously with a single 10 mg/kg dose of Compound A (FIG. 3A), a single 10 mg/kg dose of Compound C (FIG. 3B), or a 100 mg/kg dose of Compound B twice daily for four days (FIG. 3C). As shown in FIGS. 3A and 3B, serum samples were collected at 2 and 11 days post injection. As shown in FIG. 3C, serum samples were collected at 2 hours, 12 hours, and 11 days post last injection. All serum samples were analyzed via a multiplexed bead-based RodentMAP immunoassay on a Luminex instrument to determine quantities of sVCAM in rat serum. Statistics were performed with one-way ANOVA. All three alpha-4 integrin inhibitors down-regulated sVCAM in normal rats (*p<0.05; p<0.01; *p<0.001).

Example 3—Alpha-4 Integrin Inhibition Specifically Reduces sVCAM in Normal Mice (w/ Small Molecule Inhibitors)

Figure 4:
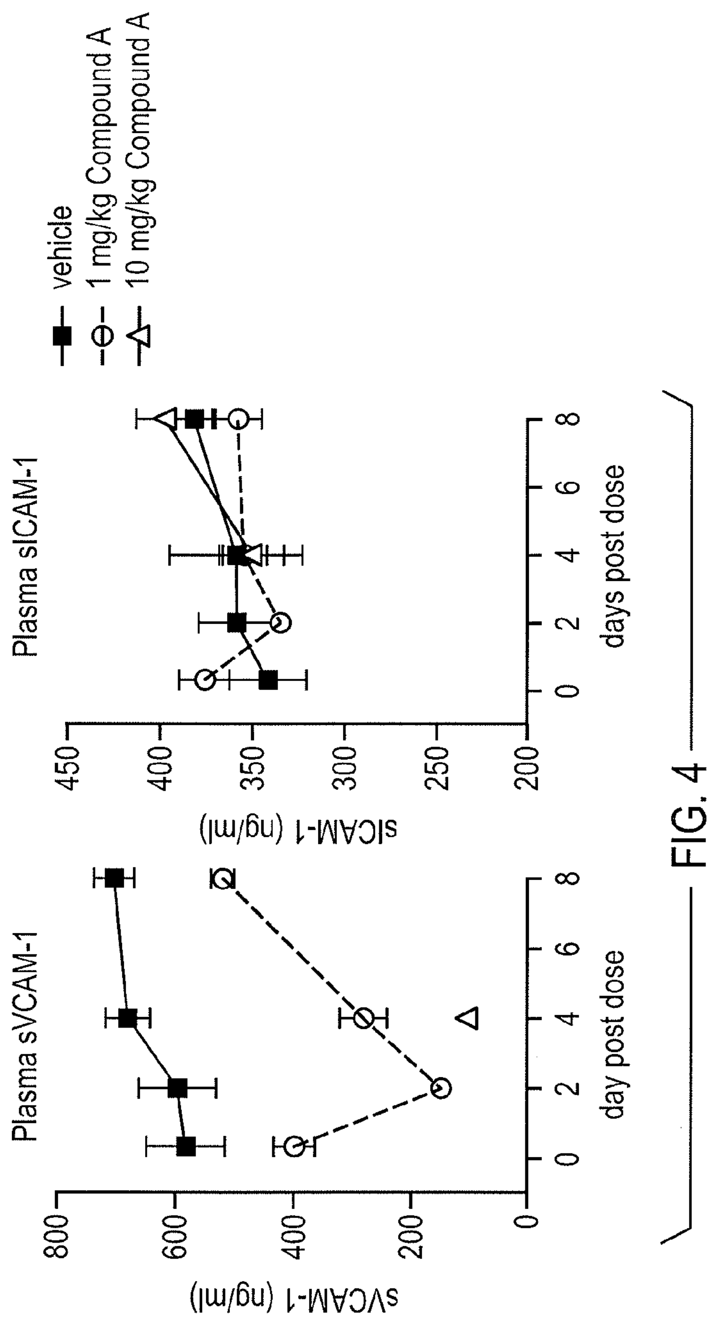
FIG. 4 depicts decreased levels of sVCAM in normal mice treated with small molecule alpha-4 integrin inhibitors. The treatment of normal mice with alpha-4 integrin inhibitors does not appear to affect soluble intracellular adhesion molecule (sICAM) level. Experiments were performed as described in Example 3.

To determine whether alpha-4 integrin inhibition resulted in the specific down-regulation of the soluble form of its ligand (i.e., sVCAM), and not the soluble form of an adhesion molecule that is not an alpha-4 integrin ligand (i.e., ICAM-1), normal mice were tested for modulation of both adhesion molecules after treatment with an alpha-4 integrin inhibitor. Balb/c mice were given a single subcutaneous injection of Compound A (1 mg/kg or 10 mg/kg) or vehicle (PBS). Plasma samples were taken at 8 hours, 2 days, 4 days, and 8 days post-dose. Plasma samples were analyzed by ELISA for soluble VCAM-1 and soluble ICAM-1 using commercially available kits (R & D Systems, Minneapolis, MN) (n=4 mice/group/time point). As shown in FIG. 4, the effect of alpha-4 integrin inhibition appeared to be specific to the soluble form of its ligand (sVCAM) and not the soluble form of an adhesion molecule that is not a ligand for alpha-4 integrin (sICAM).

Figure 5B:
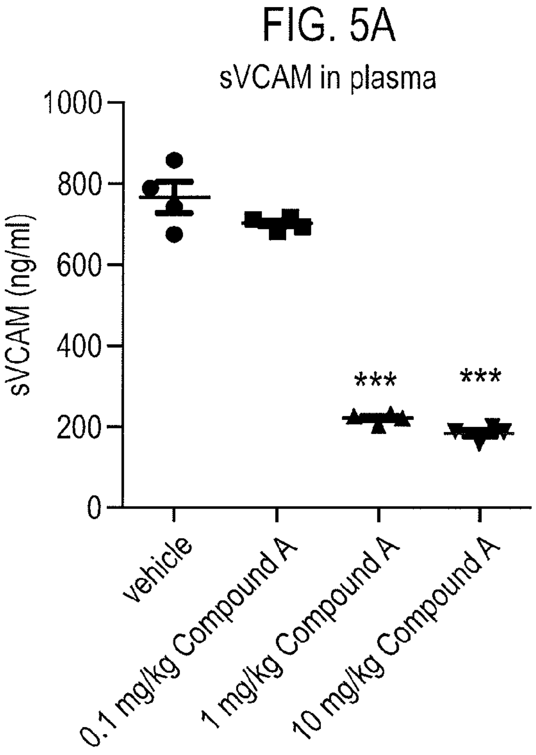
Figure 5C:
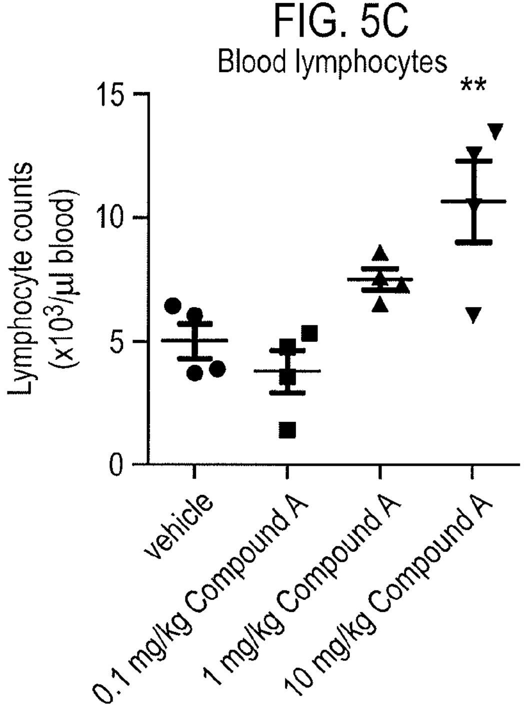
Figure 5D:
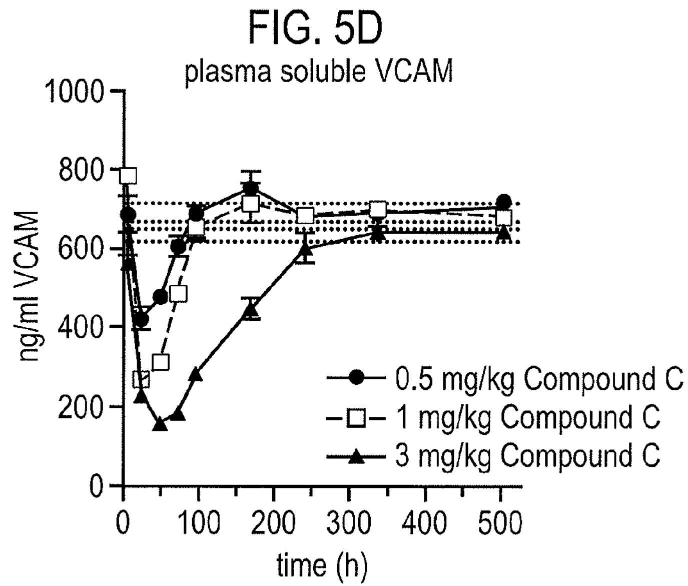
Figure 5E:
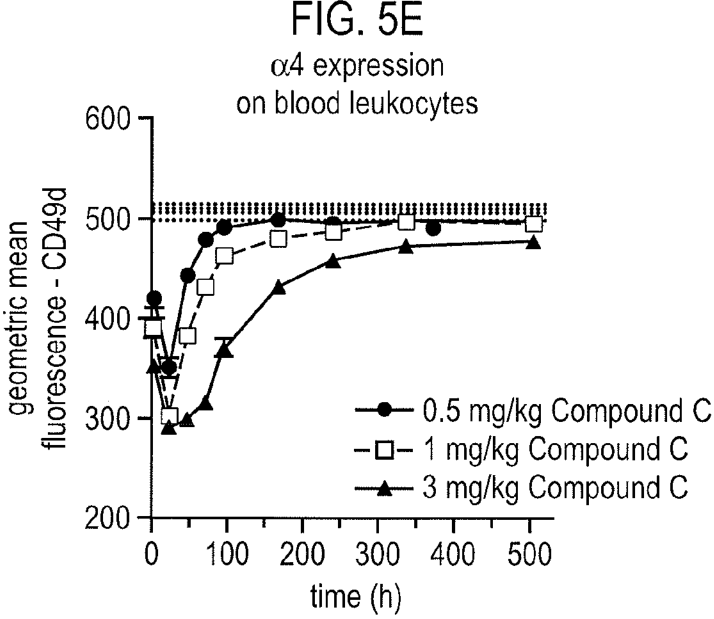
Figure 5F:
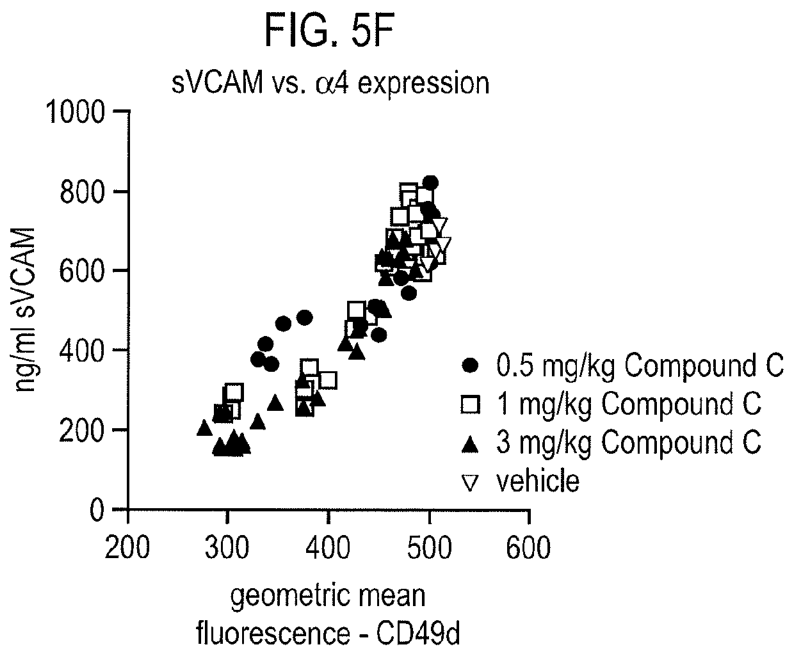

Example 4—the Effect of Alpha-4 Integrin Inhibitors on sVCAM Down-Regulation is Dose-Dependent and Correlates with Other Markers of Alpha-4 Integrin Inhibition Alpha-4 integrin inhibition results both in an increase in the number of circulating lymphocytes and down-regulation of alpha-4 integrin on the surface of circulating leukocytes. The correlation of sVCAM levels with alpha-4 integrin expression and blood lymphocyte count after alpha-4 integrin inhibitor was tested, as well as the dose-dependency of each parameter. As shown in FIG. 5A-C, Balb/c mice were dosed subcutaneously with 0.1, 1, or 10 mg/kg Compound A or vehicle (PBS). Two days after dosing, animals were euthanized and blood was taken in order to analyze sVCAM levels, alpha-4 integrin expression on the surface of leukocytes, and the number of lymphocytes in the blood. Plasma samples were analyzed for sVCAM content using ELISA (R & D Systems, Minneapolis, MN) (FIG. 5A). From the same animals, an aliquot of whole blood was stained with AlexaFluor647-labeled anti-mouse CD49d (alpha-4 integrin) antibody (Biolegend, San Diego, CA), red blood cells were lysed (FACS lysing solution, BD Biosciences, San Jose, CA), and analyzed for shifts in mean fluorescence intensity using a BD FACScan flow cytometer (FIG. 5B). From the same animals, whole blood samples were analyzed for the number of lymphocytes using a Cell Dyn Hematology analyzer (Abbott Diagnostics, Illinois) (FIG. 5C). One-way ANOVA was used to determine statistical significance. As shown in FIG. 5D-F, C57BL/6 mice were dosed subcutaneously with 0.5, 1, or 3 mg/kg Compound C or vehicle. Blood was taken at 4 hrs and 1, 2, 3, 4, 7, 10, 14, and 21 days post-dose. Plasma soluble VCAM levels (FIG. 5D) and alpha-4 integrin expression on blood leukocytes (FIG. 5E) was analyzed as described above. Respective levels in vehicle (PBS)-treated animals sampled at on day 2 post dose are indicated by dotted lines. FIG. 5F shows the correlation between sVCAM and alpha-4 integrin expression on a per-animal basis from the day 1-21 time points (n=4 mice/group/time point). sVCAM down-regulation by alpha-4 integrin inhibitors proved to be dose-dependent and correlated well with both alpha-4 integrin expression on the surface of leukocytes as well as blood lymphocyte counts (*p<0.05; p<0.01; *p<0.001).

Figure 6A:
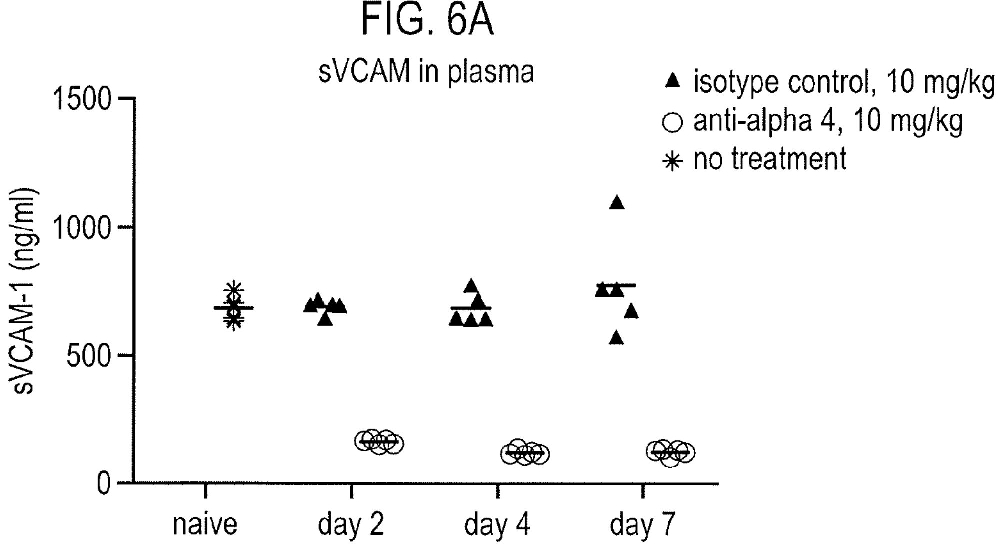
FIG. 6A-6B depicts decreased levels of sVCAM in mice treated with an antibody inhibitor of alpha-4 integrin. Experiments were performed as described in Example 5.
Figure 6B:
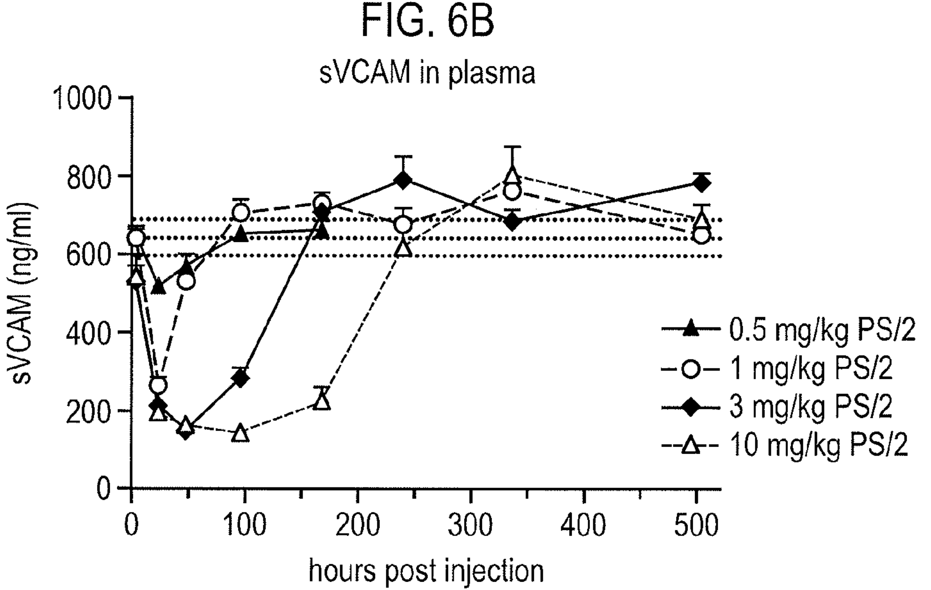

Example 5—Soluble VCAM is Also Reduced Using an Antibody Inhibitor of Alpha-4 Integrin To demonstrate the effect of alpha-4 integrin inhibition on sVCAM levels is not unique to small molecule inhibitors of alpha-4 integrin, an antibody inhibitor of alpha-4 integrin was tested for its ability to modulate sVCAM levels. As shown in FIG. 6A, Balb/c mice were given a single 10 mg/kg intraperitoneal dose of a rat anti-mouse alpha-4 integrin antibody (clone PS/2) or a rat IgG2b isotype control antibody. Blood was sampled prior to dosing (naïve) and on days 2, 4, and 7 post-dose, and analyzed for soluble VCAM by ELISA. A 10 mg/kg dose of PS/2, but not isotype control, elicited a sustained down-regulation of sVCAM in plasma. As shown in FIG. 6B, a follow-on study was performed to assess dose and time-dependency of sVCAM down-regulation by an antibody inhibitor of alpha-4 integrin. C57BL/6 mice were treated intraperitoneally with a 0.5, 1, 3, or 10 mg/kg dose of PS/2 or a 10 mg/kg dose of a rat IgG2b isotype control antibody. Plasma samples were collected at 4 hours and 1, 2, 4, 7, 10, 14, and 21 days post-dose and analyzed for sVCAM levels. The data as shown in FIG. 6 indicate that sVCAM down-regulation is dependent on the dose of PS/2, and sVCAM levels recover over time. Dotted lines indicate individual levels of sVCAM on day 2 in mice treated with isotype control antibody (n=4 mice/group/time point).

Figures 7A, 7B:
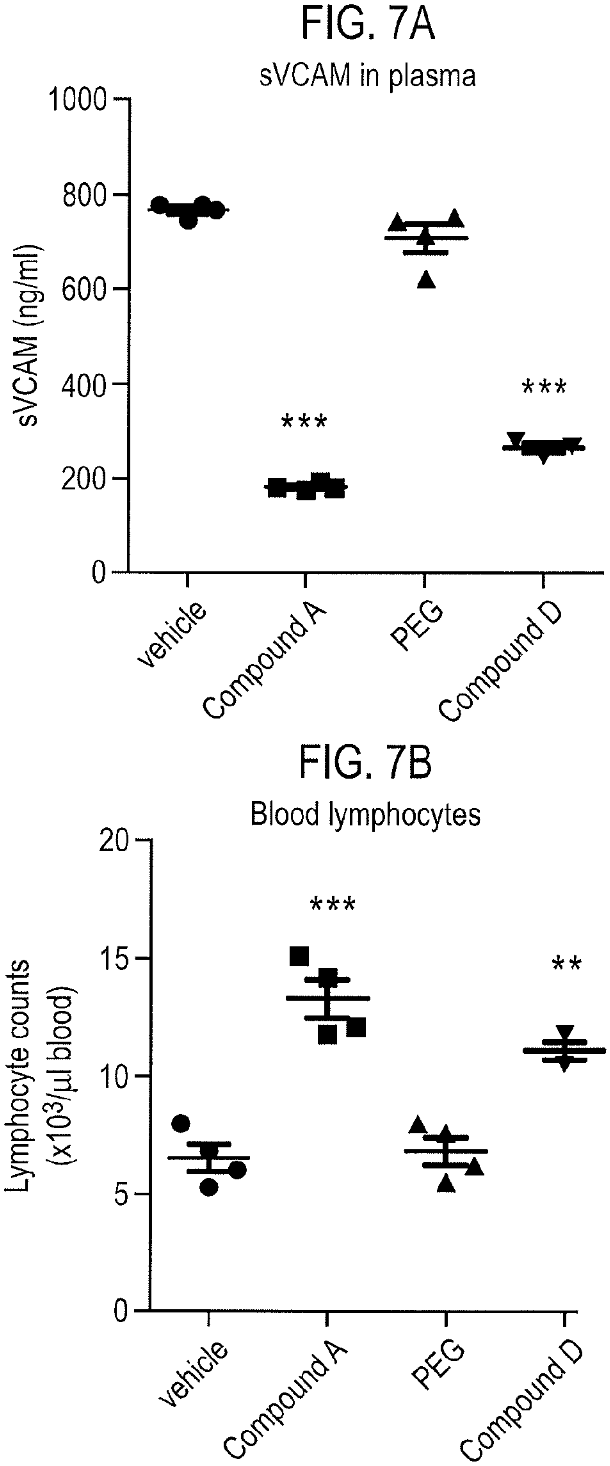
FIG. 7A-7B depicts decreased levels of sVCAM in mice treated with a non-pegylated small molecule inhibitor of alpha-4 integrin. Experiments were performed as described in Example 6.

Example 6—sVCAM Levels are Down-Regulated by a Non-Pegylated Small Molecule Inhibitor of Alpha-4 Integrin. sVCAM Levels are not Affected by PEG Alone To demonstrate the effect of alpha-4 integrin inhibition on sVCAM levels is not limited to pegylated small molecule inhibitors, nor is elicited by PEG itself, normal mice were dosed with Compound D (a non-pegylated alpha-4 integrin inhibitor) and the PEG backbone on which Compound A is built. Balb/c mice were given a single subcutaneous dose of vehicle (PBS), a single subcutaneous dose of Compound A (10 mg/kg), a single subcutaneous dose of the PEG backbone on which Compound A is built (10 mg/kg), or 5 subcutaneous doses of Compound D (50 mg/kg) every 12 hours. Two days after Compound A and PEG injection, and 4 hours after the final Compound D injection, blood was sampled. sVCAM was measured by ELISA (R & D Systems) (FIG. 7A) and blood lymphocytes were quantitated using a Cell-Dyn Hematology analyzer (Abbott Diagnostics) (FIG. 7B). Statistics were performed using one-way ANOVA and statistically significant differences compared to vehicle treated animals are denoted. Both Compound A and Compound D, but not PEG, were able to elicit increased blood lymphocytes and down-regulate sVCAM in plasma (*p<0.05; p<0.01; *p<0.001).

Figure 8A:
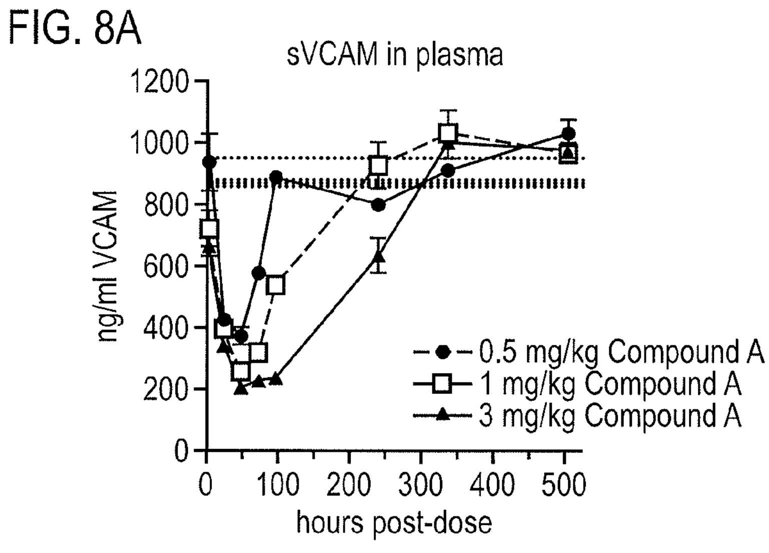
FIG. 8A-8C depicts that the effects of alpha-4 integrin inhibition on sVCAM levels is dose-dependent and wears off as plasma levels of the alpha-4 integrin inhibitor declines. Experiments were performed as described in Example 7.
Figure 8B:
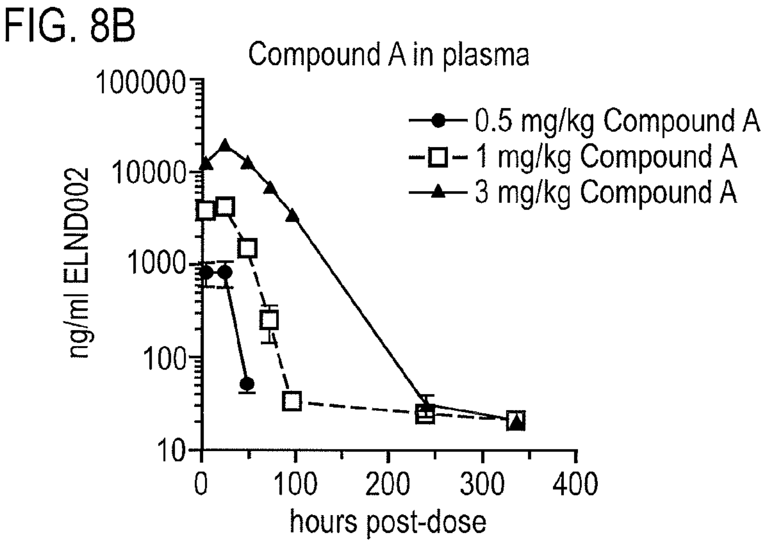
Figure 8C:
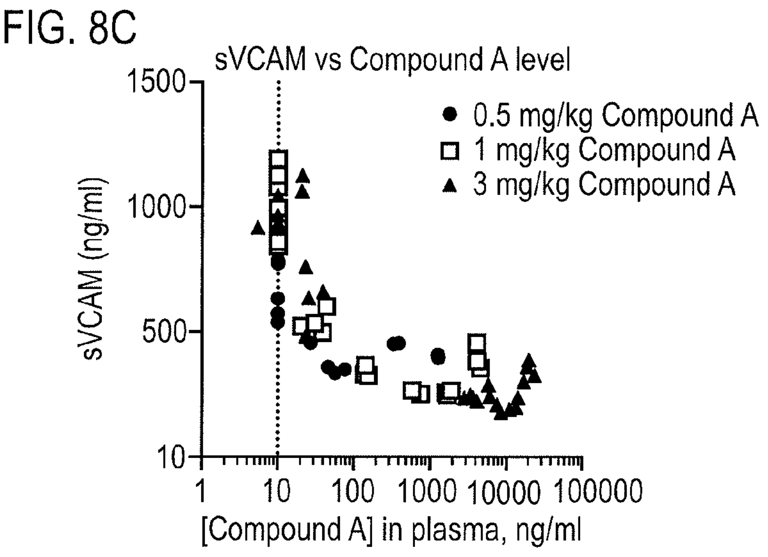

Example 7—the Effects of Alpha-4 Integrin Inhibition on Soluble VCAM Levels is Dose Dependent and Wears Off as Plasma Levels of Alpha-4 Integrin Inhibitor Decline To determine whether the regulation of sVCAM by alpha-4 integrin inhibitors is related to circulating drug level, and whether the effect on sVCAM is reversible, these parameters were measured over a three week period after dosing normal mice. C57BL/6 mice were dosed subcutaneously with a single 0.5, 1, or 3 mg/kg dose of Compound A or vehicle (PBS). Blood was sampled at four hours and 1, 2, 3, 4, 10, 14, and 21 days post-dose and analyzed for sVCAM levels in plasma by ELISA (dotted lines indicate vehicle control levels at day 2) (FIG. 8A) and Compound A levels in plasma using an LC/MS/MS method (FIG. 8B). The limit of detection for Compound A using this method is 10 ng/ml. sVCAM and Compound A levels from days 1-21 were plotted on a per-mouse basis to demonstrate correlation (FIG. 8C). In samples where Compound A was undetectable, a value of 10 ng/ml was assigned (n=4 mice/group/time point). sVCAM levels correlated well with circulating drug level, and returned to baseline as drug levels became undetectable in plasma (*p<0.05; p<0.01; *p<0.001).

Example 8—sMAdCAM is Down-Regulated when Alpha-4 Integrin is Inhibited in Mouse Models of Colitis Compound C is a pegylated small molecule inhibitor of both alpha-4 beta-1 integrin and alpha-4 beta-7 integrin. PS/2 is a rat anti-mouse alpha-4 integrin blocking antibody. Both these alpha-4 integrin inhibitors were administered to mice with induced forms of colitis. Serum samples were tested for sMAdCAM levels by ELISA (R & D Systems, Minneapolis, MN). In the first mouse model of colitis, CD45RBhi CD4+ cells were isolated from Balb/c spleens via magnetic bead activated cell sorting for CD4+ cells (untouched CD4+ cell isolation kit, Miltenyi Biotec) followed by fluorescence-activated cell sorting for CD45RBhi cells. CD4+CD45RBhi cells were injected intraperitoneally into SCID mice. Symptoms of colitis began to appear one week post cell transfer. Eight weeks after transfer, animals were treated with either vehicle (PBS) or Compound C (10 mg/kg) every 3 days for a period of 15 days. At this time, animals were sacrificed and serum samples were analyzed for sMAdCAM. The results are presented in FIG. 9A. Statistics shown are in comparison to the CD45RBhi transfer+vehicle group. Transfer of cells significantly increased the amount of circulating sMAdCAM. The data shown in FIG. 9A indicate that treatment with Compound C statistically significantly reduced sMAdCAM levels.

In a second mouse model, chronic colitis was induced in Balb/c mice via administering 4% Dextran Sulphate Sodium (DSS) in their drinking water for 7 days followed by 7 days of tap water. This cycle was repeated four times. Mice displayed symptoms of colitis during each DSS cycle. On day 56, mice entered a chronic disease state and began treatment with either vehicle (PBS) or Compound C (10 mg/kg) every 3 days for 15 days. At this time, animals were sacrificed and serum samples were analyzed for sMAdCAM. The results are presented in FIG. 9B. Statistics shown are in comparison to sMAdCAM levels in naïve mice. The data shown in FIG. 9B indicate that (1) DSS induced a statistically significant increase in the amount of sMAdCAM in the serum, and (2) treatment with Compound C statistically significantly reduced sMAdCAM levels.

Figures 9A, 9B, 9C:
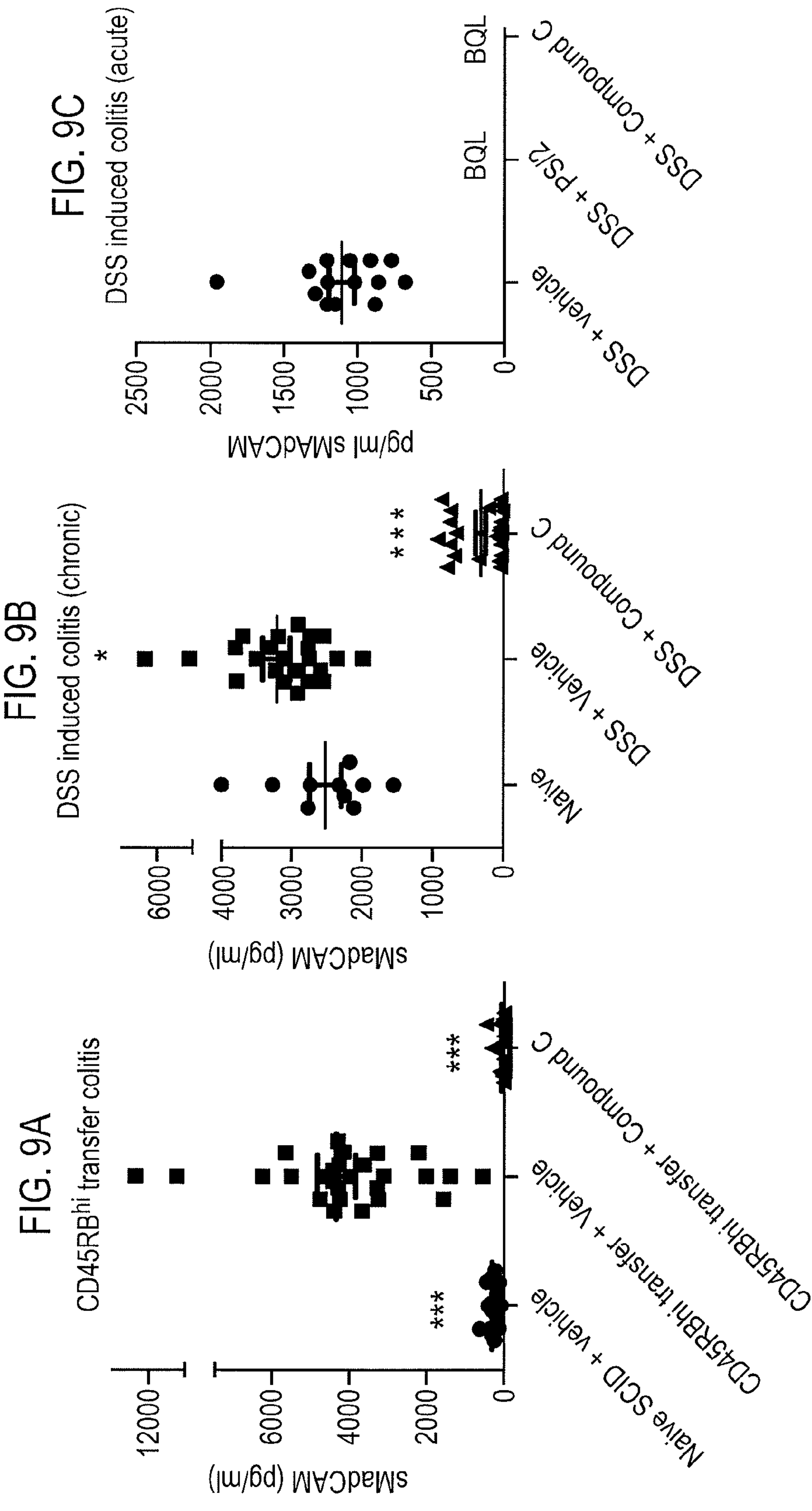
FIG. 9A-9C depicts that alpha-4 integrin inhibition results in down-regulation of sMAdCAM in several mouse models of colitis. Experiments were performed as described in Example 8.

In a third mouse model, Balb/c mice were administered 3% DSS in their drinking water for κ days to induce acute colitis. On day 6, water was switched to tap water and animals were dosed with Compound C (10 mg/kg every 3 days) or PS/2 (10 mg/kg every 5 days). Serum was collected on day 14 and samples were analyzed for sMAdCAM. The results were presented in FIG. 9C. In both treatment groups, the level of sMAdCAM was below the quantitation limit (BQL) of the assay (FIG. 9C). These experiments demonstrate that alpha-4 integrin inhibition in mouse models of colitis results in statistically significant down-regulation of sMAdCAM levels (*p<0.05; p<0.01; *p<0.001).

Figure 10:
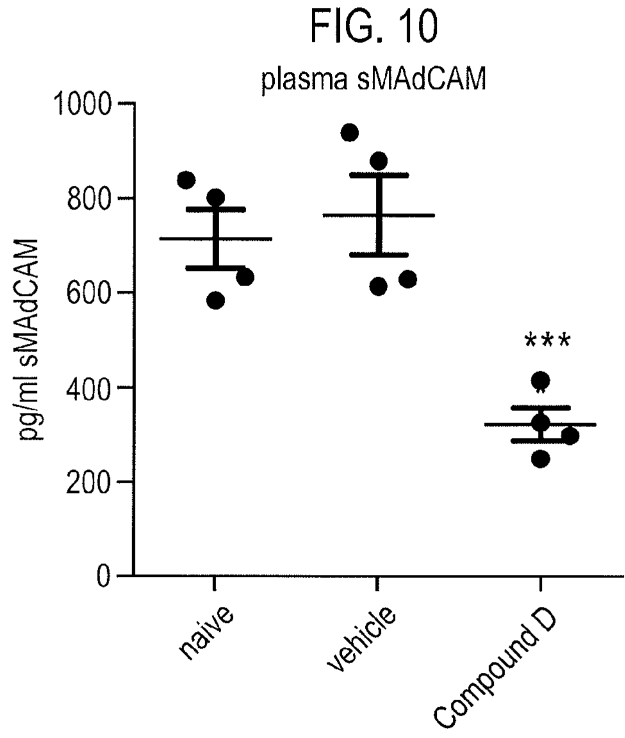
FIG. 10 depicts that alpha-4 integrin inhibition by a small molecule inhibitor results in down-regulation of sMAdCAM in normal mice. Experiments were performed as described in Example 9.

Example 9—sMAdCAM is Down-Regulated when Alpha-4 Integrin is Inhibited in Normal Mice with a Small Molecule Inhibitor Compound D is a small molecule inhibitor of alpha-4 integrin and was tested for its ability to down-regulate sMAdCAM in the plasma of normal mice. Balb/c mice were administered subcutaneously 50 mg/kg Compound D or vehicle (PBS) every 12 hours. Four hours after the 5th dose, plasma was sampled and analyzed for sMAdCAM by ELISA. The results as shown in FIG. 10 indicate that Compound D treatment results in statistically significant down-regulation of sMAdCAM in plasma (*p<0.05; p<0.01; *p<0.001).

Figure 11:
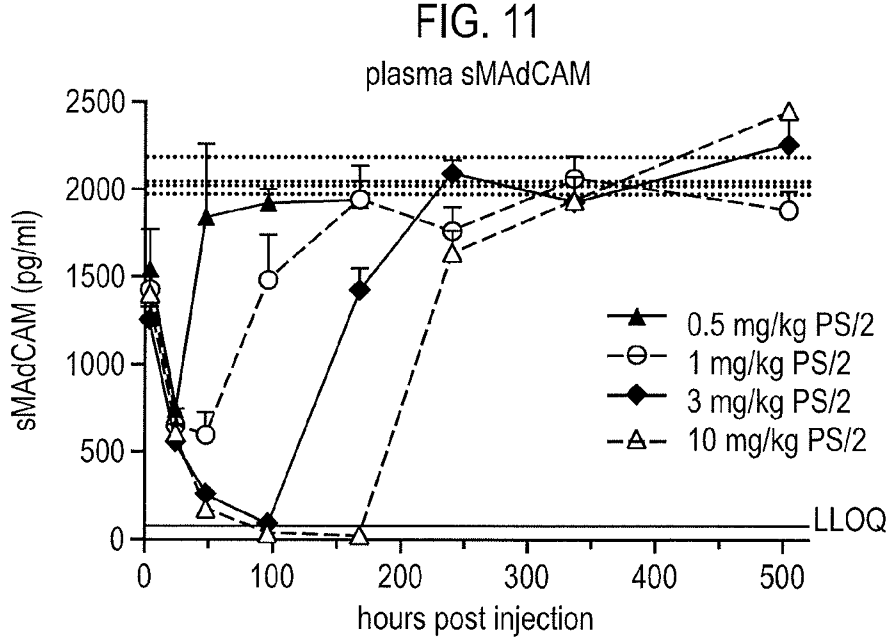
FIG. 11 depicts that alpha-4 integrin inhibition by an antibody inhibitor results in down-regulation of sMAdCAM in normal mice. Experiments were performed as described in Example 10.

Example 10—an Antibody Inhibitor of Alpha-4 Integrins Also Results in sMAdCAM Down-Modulation in Normal Mice To test whether an antibody inhibitor of alpha-4 integrin can modulate sMAdCAM levels, to test dose-dependency, and to measure the ability of sMAdCAM levels to recover after alpha-4 integrin inhibition, PS/2 was administered intraperitoneally to C57BL/6 mice at 0.5, 1, 3, and 10 mg/kg and plasma was sampled at four hours and 1, 2, 4, 7, 10, 14, and 21 days post dose. As a control, a rat IgG2b isotype control antibody was dosed at 10 mg/kg intraperitoneally and plasma was sampled at day 2. sMAdCAM levels in plasma samples were measured by ELISA (FIG. 11). Dotted lines indicate the sMAdCAM levels present in the 4 isotype control treated mice at day two (n=4 mice/group/timepoint; LLOQ=lower limit of quantitation of the ELISA assay). The data as shown in FIG. 4 demonstrate that an antibody inhibitor of alpha-4 integrin dose-dependently modulates sMAdCAM levels.

Example 11—Down-Regulation of sMAdCAM by Alpha-4 Integrin Inhibitors is Dose Dependent, Reversible, and Correlates with In Vitro Selectivity of the Alpha-4 Integrin Inhibitor for the a4b7 Integrin Heterodimer Alpha-4 integrin forms heterodimers with either beta-1 or beta-7 integrins. MAdCAM is a ligand for alpha-4 beta-7 ($\alpha 4\beta 7$) while VCAM is a ligand for alpha-4 beta-1 ($\alpha 4\beta 1$). Alpha-4 integrin inhibitors can display different selectivity for $\alpha 4\beta 7$ and $\alpha 4\beta 1$. To test the whether the in vitro selectivity of alpha-4 inhibitors for $\alpha 4\beta 7$ correlates with in vivo down-regulation of sMAdCAM, experiments were conducted using two alpha-4 integrin inhibitors that display different selectivity for $\alpha 4\beta 7$. Compound C and Compound A are both pegylated small molecule inhibitors of alpha-4 integrin.

Figures 12A, 12B:
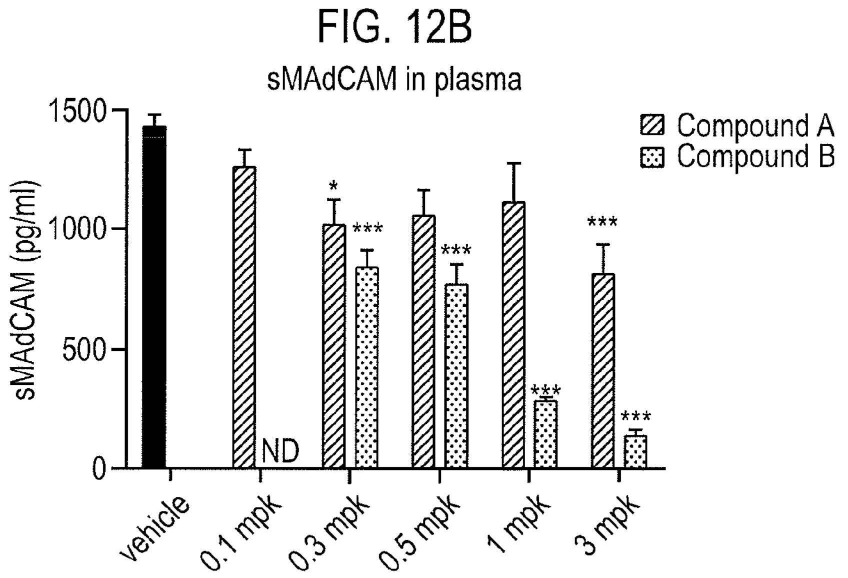
FIG. 12A-12F depicts that down-regulation of sMAdCAM by alpha-4 integrin inhibitors is dose-dependent, reversible, and correlates with in vitro selectivity of the alpha-4 integrin inhibitor for the alpha-4 beta-7 integrin heterodimer. Experiments were performed as described in Example 11.

FIG. 12A depicts the in vitro selectivity of these compounds for $\alpha 4\beta 1$ and $\alpha 4\beta 7$. The induction of $\alpha 4\beta 1$ and $\alpha 4\beta 7$-specific epitopes by the compounds was measured using the following assay. Lymphocytes isolated from human blood by Ficoll gradient were incubated with a titration of Compound A or Compound C in PBS with 5% FBS and either 10 mg/ml 2G3 (ligand induced anti-beta-7 antibody) or 15/7 (ligand induced anti-beta-1 antibody). After incubation with a PE-conjugated anti-mouse IgG secondary antibody, epitope induction was measured by flow cytometry. Data are expressed as binding. The data as shown in FIG. 12A indicate that (1) Compound C binds to both $\alpha 4\beta 1$ and $\alpha 4\beta 7$ integrin with equal potency; and (2) Compound A is 100-fold more selective in binding to $\alpha 4\beta 1$ over $\alpha 4\beta 7$.

To investigate whether in vitro selectivity translated to differential down-regulation of sMAdCAM in vivo, Compound A and Compound C were administered subcutaneously to C57BL/6 at 0.1, 0.3, 0.5, 1, and 3 mg/kg. At 48 hours post dose, plasma was collected and sMAdCAM was quantitated. The results are presented in FIG. 12B. Compound C appears more potent than Compound A in down-regulating sMAdCAM, suggesting that selectivity for $\alpha 4\beta 7$ is mediating the effect on the soluble form of its ligand. Significance was calculated via one-way ANOVA and compared to vehicle control (*$p<0.05$; $p<0.01$; *$p<0.001$, n=4 mice/group, ND=not done).

Figure 12C:
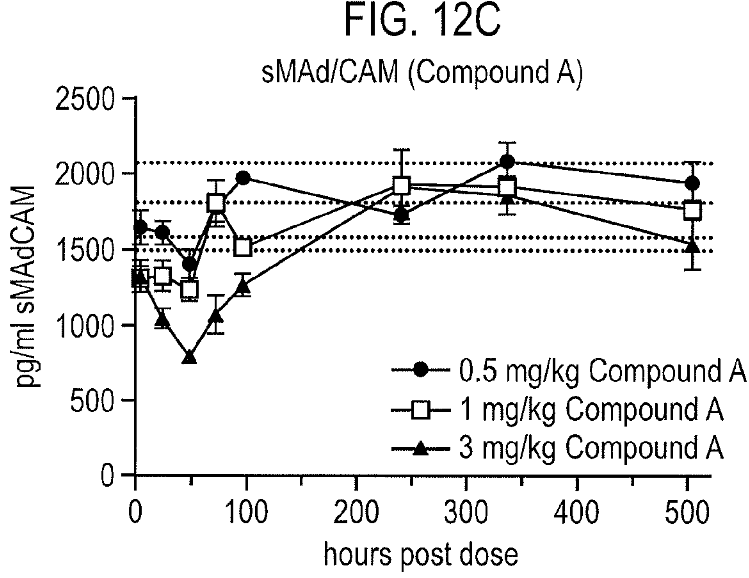
Figure 12D:
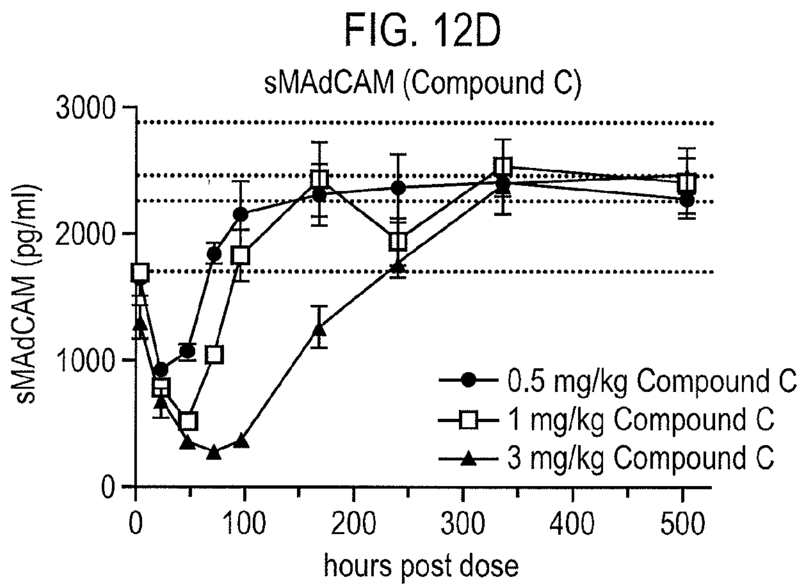

In order to measure the dose/time relationship of sMAdCAM down-regulation by $\alpha 4\beta 7$ inhibition, both Compound A (FIG. 12C) and Compound C (FIG. 12D) were dosed subcutaneously to C57BL/6 mice at 0.5, 1, and 3 mg/kg, and plasma was collected at 4 hrs and 1, 2, 3, 4, 7, 10, 14, and 21 days post-dose. Dotted lines indicate the sMAdCAM levels in vehicle treated animals at day 2 (n=4 mice/group/time point). As shown in FIG. 12D, Compound C, the pan-alpha-4 integrin inhibitor, down-regulated sMAdCAM to a greater extent than Compound A that is a selective $\alpha 4\beta 1$ inhibitor. This suggests $\alpha 4\beta 7$ inhibition is necessary to evoke sMAdCAM down-regulation. Additionally, MAdCAM levels recover to baseline levels over time.

Figure 12E:
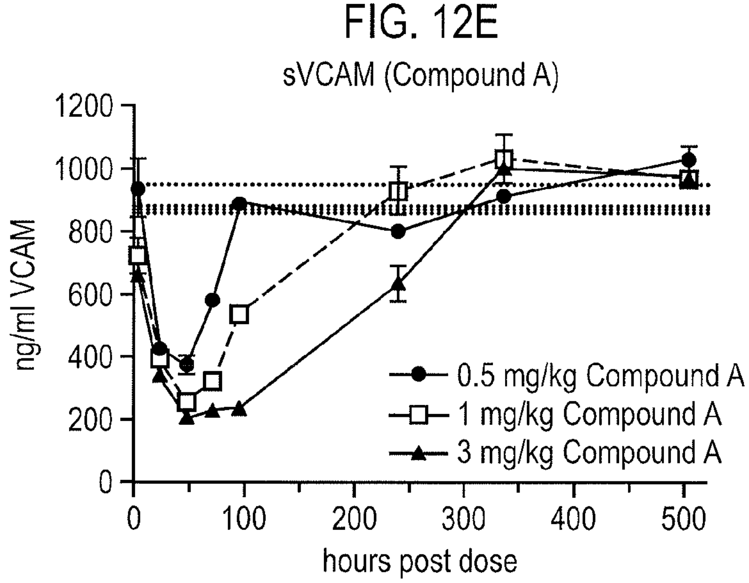
Figure 12F:
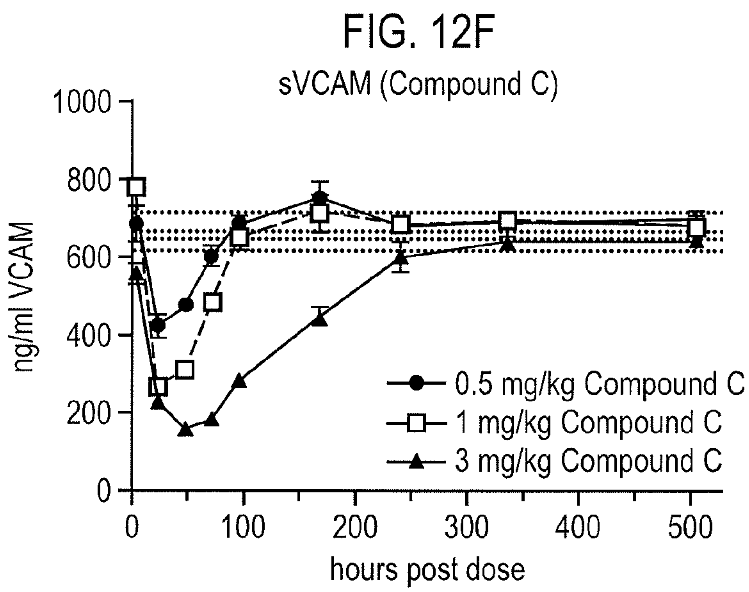

As shown in FIGS. 12E and 12F, sVCAM was measured in samples taken from the same animals as above via ELISA (R & D Systems). Dotted lines indicate the sVCAM levels in vehicle treated animals at day 2 (n=4 mice/group/time point). Both Compound A and Compound C were similarly potent in down-regulating sVCAM in plasma samples, evoking the similar selectivity of these compounds for $\alpha 4\beta 1$, the VCAM ligand. Overall, these data indicate that in vitro selectivity for $\alpha 4\beta 7$ or $\alpha 4\beta 1$ is mirrored in vivo via down-regulation of sMAdCAM or sVCAM, respectively.

The selectivity of Compound A as discussed above was further verified in human subjects. For this, forty-one individuals were administered orally with Compound A at 0.5 mg/kg. Whole blood was collected at various time points post dose (up to 28 days post dose). Both sVCAM and sMAdCAM levels were quantitated by ELISA as described above. Compound A was known to block the binding of 9F10 to alpha-4 integrins. The expression levels of $\alpha 4\beta 1$ and $\alpha 4\beta 7$ were determined by measuring mean fluorochrome intensity (MFI) of white blood cells incubated with a fluorescent-labeled 9F10 (a mouse anti-human alpha-4 integrin antibody). It was also known that Compound A, upon its binding to integrin receptors, induces the expression of specific ligand-induced binding site epitopes on $\beta 1$ and $\beta 7$ subunits, which are recognized by mouse monoclonal antibodies 15/7 and 2G3 (as described above). The saturation levels of $\alpha 4\beta 1$ and $\alpha 4\beta 7$ were determined using fluorescence-labeled 15/7 and 2G3 antibodies, and calculated as follows:

$$\%\ \text{saturation} = \frac{\text{MFI\_of\_test\_sample} - \text{MFI\_background}}{\text{MFI\_of\_saturated\_control} - \text{MFI\_background}}$$

Figures 13A, 13B, 13C:
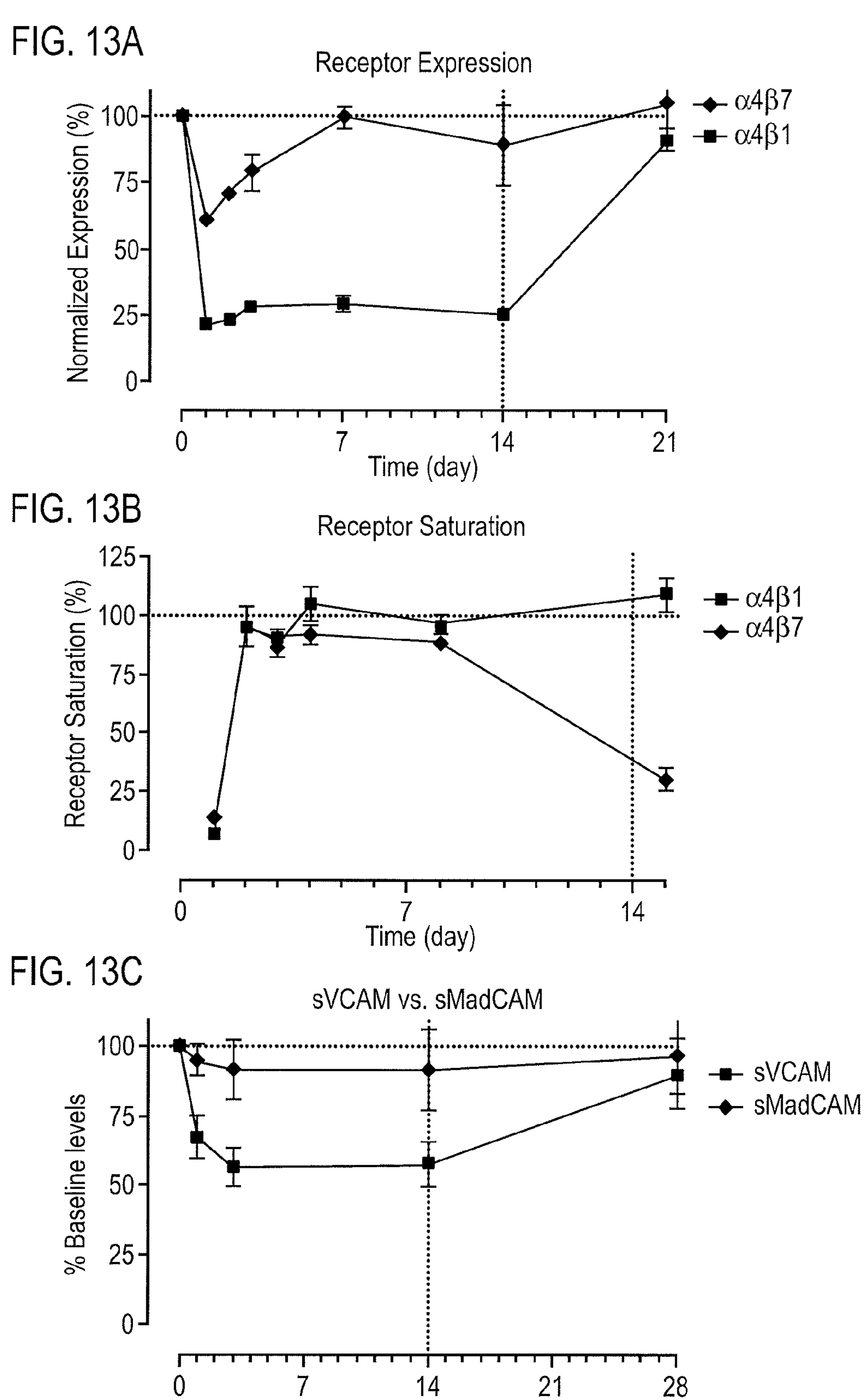
FIG. 13A-13C depicts selective down-regulation of sVCAM by an alpha-4 integrin inhibitor selectively binding to the alpha-4 beta-1 integrin heterodimer. Experiments were performed as described in Example 11.

The data are presented in FIG. 13. FIG. 13A indicates that administering Compound A in human subjects results in a marked decrease of $\alpha 4\beta 1$ expression levels from as early as 1 day post dose to at least 14 days post dose. The $\alpha 4\beta 1$ levels return to the base level about 7 days post dose. FIG. 13B shows that $\alpha 4\beta 1$ becomes saturated about two days after administering Compound A, and the saturation lasts at least another 13 days (15 days post dose). The saturation levels of $\alpha 4\beta 7$, however, drops significantly 8 days after administration. As shown in FIG. 13C, the sVCAM levels decrease significantly 1 day after administration, and start returning to the base line (prior to administration) 14 days after administration. The sMAdCAM levels, however, remain close to the base level even 28 days after administration. These data are consistent with the above in vitro observation that Compound A is more selective in binding to $\alpha 4\beta 1$ over $\alpha 4\beta 7$.

Figure 14:
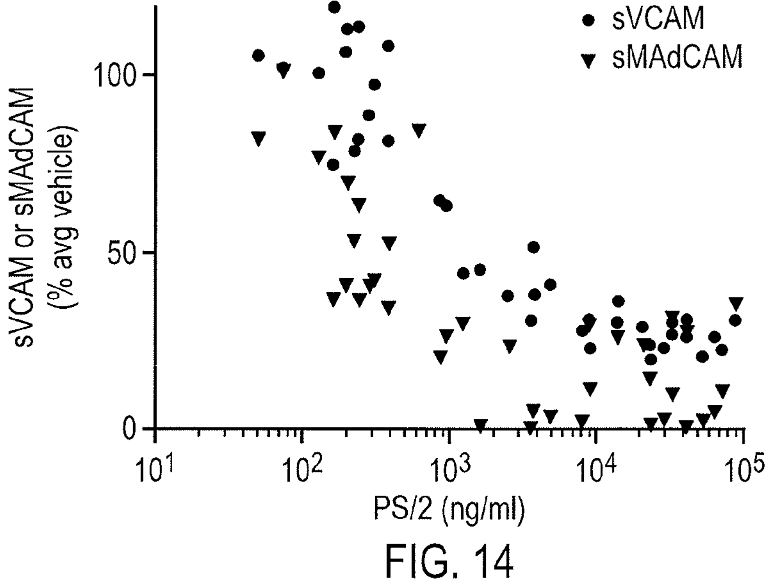
FIG. 14 depicts the correlation between the sVCAM/sMAdCAM levels and the alpha-4 integrin antibody levels in mice. Experiments were performed as described in Example 12.

Example 12—Correlation Between the Alpha-4 Integrin Inhibitor Levels and the sVCAM/sMAdCAM Levels in Mice Thirty-eight (38) mice (C57BL/6) were administered intraperitoneally with various amounts of PS/2 (an anti-alpha-4 integrin antibody). Plasma samples were collected at various time points post-dose. The sVCAM levels, the sMAdCAM levels, and PS/2 levels in the plasma samples were analyzed by ELISA methods as described in the above examples. The sVCAM and sMAdCAM levels (% average vehicle) are plotted against the PS/2 concentrations, as shown in FIG. 14. The results indicate strong negative linear correlations for both sVCAM ($r=-0.61$; $p<0.0001$) and sMAdCAM ($r=-0.42$; $p<0.0041$), namely, the higher concentration of the anti-alpha-4 integrin antibody (corresponding to a higher level of inhibition of alpha-4 integrins), the lower level of sVCAM or sMAdCAM.

Various modifications and variations of the described methods and system of the disclosure will be apparent to those skilled in the art without departing from the scope and spirit of the disclosure. Although the disclosure has been described in connection with specific representative embodiments, it should be understood that the subject matters as claimed should not be unduly limited to such specific embodiments. Indeed, various modifications of the described modes for carrying out the disclosure that are obvious to those skilled in the art are intended to be within the scope of the following claims.

Embodiments of the present disclosure provide a method of monitoring the change of the alpha-4 integrin activities in an individual by correlating with the soluble vascular cell adhesion molecule (sVCAM) and/or soluble mucosal addressin cell adhesion molecule (sMAdCAM) levels.

For example, embodiments of the present disclosure (1) provide an in vitro method of determining a difference in alpha-4 integrin activity in an individual, comprising: a) measuring a soluble molecule in a first biological sample obtained from the individual immediately before administration of an alpha-4 integrin inhibitor; b) measuring the soluble molecule in a second biological sample, wherein the second biological sample has been obtained from the individual within thirty-one days after administration of the alpha-4 integrin inhibitor; and c) determining whether there is a decrease in the levels of the soluble molecule between the first and second biological samples, wherein the decrease correlates with a decrease in alpha-4 integrin activity in the individual, and thereby determining whether there is a difference in alpha-4 integrin activity in the individual after administration of the alpha-4 integrin inhibitor compared with before administration of the alpha-4 integrin inhibitor, and wherein the soluble molecule is sVCAM and/or sMAdCAM.

(2) Embodiments of the present disclosure also provide a method of the above (1), further comprising detecting a decrease in the levels of the soluble molecule in the second biological sample compared with the first biological sample, and attributing said decrease to a decrease in alpha-4 integrin activity in the individual after administration of the alpha-4 integrin inhibitor compared with before administration of the alpha-4 integrin inhibitor.

(3) Embodiments of the present disclosure also provide a method of the above (1) or (2), wherein alpha-4 integrin activity is alpha-4 beta-1 integrin activity, and wherein the soluble molecule is sVCAM.

(4) Embodiments of the present disclosure also provide a method of the above (1) or (2), wherein alpha-4 integrin activity is alpha-4 beta-7 integrin activity, and wherein the soluble molecule is sMAdCAM.

(5) Embodiments of the present disclosure also provide a method of any of the above (1)-(4), wherein the individual has a disease or disorder associated with a pathological or chronic inflammation.

(6) Embodiments of the present disclosure also provide a method of the above (5), wherein the disease or disorder is selected from the group consisting of multiple sclerosis (MS), meningitis, encephalitis, inflammatory bowel disease, rheumatoid arthritis (RA), asthma, acute juvenile onset diabetes, AIDS dementia, atherosclerosis, nephritis, retinitis, atopic dermatitis, psoriasis, myocardial ischemia, chronic prostatitis, complications from sickle cell anemia, lupus erythematosus, and acute leukocyte-mediated lung injury.

(7) Embodiments of the present disclosure also provide a method of any of the above (1)-(6), wherein the alpha-4 integrin inhibitor is an antibody.

(8) Embodiments of the present disclosure also provide a method of any of the above (1)-(7), wherein the first and/or the second biological sample is selected from the group consisting of a tissue, a cell, and a body fluid.

(9) Embodiments of the present disclosure also provide a method of the above (8), wherein the first and/or the second biological sample is a body fluid selected from the group consisting of blood, lymph, sera, plasma, urine, semen, synovial fluid, saliva, tears, bronchoalveolar lavage, and cerebrospinal fluid.

(10) Embodiments of the present disclosure also provide a method of the above (8), wherein the first and/or the second biological sample is in the form of frozen plasma or serum.

(11) Embodiments of the present disclosure also provide a method of any of the above (1)-(10), wherein the second biological sample is obtained from the individual one day after administration of the alpha-4 integrin inhibitor.

(12) Embodiments of the present disclosure also provide a method of any of the above (1)-(11), wherein the soluble molecule is measured by a method selected from the group consisting of enzyme-linked immunosorbent assays (ELISA), radioimmunoassay (MA), Western blotting, and microbead-based protein detection assay.

(13) Embodiments of the present disclosure also provide a method of any of the above (1)-(12), further comprising determining whether an adjustment in treatment of the individual is required, wherein no decrease or a statistically insignificant decrease ($p>0.05$) in the levels of the soluble molecule between the first and second biological samples indicates ineffective response to the alpha-4 integrin inhibitor requiring a treatment adjustment of the individual.

(14) Embodiments of the present disclosure also provide a method of the above (13), further comprising detecting no decrease, or detecting a statistically insignificant decrease ($p>0.05$), in the level of the soluble molecule in the second biological sample compared with the first biological sample, and concluding that a treatment adjustment of the individual is required.

(15) Embodiments of the present disclosure also provide a method of the above (13) or (14), wherein the treatment adjustment comprises changing to a different alpha-4 integrin inhibitor or increasing the dosage of the alpha-4 integrin inhibitor.

(16) Embodiments of the present disclosure also provide an in vitro use of sVCAM and/or sMAdCAM as a pharmacodynamic biomarker for the activity of (i) alpha-4 integrin or (ii) a modulator of alpha-4 integrin activity.

(17) Embodiments of the present disclosure also provide a use of the above (16), comprising in vitro use of sVCAM and/or sMAdCAM as a pharmacodynamic biomarker for said activity in an individual receiving treatment with a modulator of alpha-4 integrin activity.

(18) Embodiments of the present disclosure also provide a us of the above (17), wherein the modulator is an alpha-4 integrin inhibitor.

(19) Embodiments of the present disclosure also provide a use of the above (17), wherein the individual has a disease or disorder associated with a pathological or chronic inflammation, optionally selected from the group consisting of multiple sclerosis (MS), meningitis, encephalitis, inflammatory bowel disease, rheumatoid arthritis (RA), asthma, acute juvenile onset diabetes, AIDS dementia, atherosclerosis, nephritis, retinitis, atopic dermatitis, psoriasis, myocardial ischemia, chronic prostatitis, complications from sickle cell anemia, lupus erythematosus, and acute leukocyte-mediated lung injury.

(20) Embodiments of the present disclosure also provide a use of any of the above (16)-(19), wherein the alpha-4 integrin activity is alpha-4 beta-1 integrin activity, and wherein the pharmacodynamic biomarker is sVCAM.

(21) Embodiments of the present disclosure also provide a use of any of the above (16)-(19), wherein the alpha-4 integrin activity is alpha-4 beta-7 integrin activity, and wherein the pharmacodynamic biomarker is sMAdCAM.

What is claimed is:

1. A method of adjusting the treatment of an individual with an alpha-4 integrin inhibitor, comprising:

a) measuring a soluble molecule in a first biological sample obtained from the individual immediately before administration of a first dose of an alpha-4 integrin inhibitor, wherein the soluble molecule is soluble Vascular Cell Adhesion Molecule (sVCAM) and/or Mucosal addressin cell adhesion molecule 1 (sMAdCAM) and the alpha-4 integrin inhibitor is an anti-alpha-4 integrin antibody;

b) measuring the soluble molecule in a second biological sample, wherein the second biological sample has been obtained from the individual within 1, 2, 3 4, 5, 6, 7, 8, 9, 10, 11, 12, 13, or 14 days after administration of the first dose of the alpha-4 integrin inhibitor;

c) determining whether there is a decrease in the levels of the soluble molecule between the first and second biological samples, wherein the decrease correlates with a decrease in alpha-4 integrin activity in the individual, and thereby determining whether there is a difference in alpha-4 integrin activity in the individual after administration of the alpha-4 integrin inhibitor compared with before administration of the alpha-4 integrin inhibitor; and d) administering either an increased second dose of the same alpha-4 integrin inhibitor to the individual, or a dose of a different alpha-4 integrin inhibitor, when there is no decrease or a statistically insignificant decrease ($p>0.05$) in the levels of the soluble molecule between the first and second biological samples indicating an ineffective response to the alpha-4 integrin inhibitor, or administering the same dose of the same alpha-4 integrin inhibitor to the individual when there is a statistically significant decrease ($p<0.05$) in the levels of sVCAM and/or sMAdCAM between the first and second biological samples.

2. The method of claim 1, wherein alpha-4 integrin activity is alpha-4 beta-1 integrin activity, and wherein the soluble molecule is sVCAM, and/or wherein alpha-4 integrin activity is alpha-4 beta-7 integrin activity, and wherein the soluble molecule is SMAdCAM.

3. The method of claim 1, wherein the individual has a disease or disorder associated with a pathological or chronic inflammation.

4. The method of claim 3, wherein the disease or disorder is selected from the group consisting of multiple sclerosis (MS), meningitis, encephalitis, inflammatory bowel disease, rheumatoid arthritis (RA), asthma, acute juvenile onset diabetes, AIDS dementia, atherosclerosis, nephritis, retinitis, atopic dermatitis, psoriasis, myocardial ischemia, chronic prostatitis, complications from sickle cell anemia, lupus erythematosus, and acute leukocyte-mediated lung injury.

5. The method of claim 1, wherein the soluble molecule is measured by a method selected from the group consisting of enzyme-linked immunosorbent assays (ELISA), radioimmunoassay (RIA), Western blotting, and microbead-based protein detection assay.

6. A method of treating an individual having an autoimmune disease, comprising:

a) measuring a soluble molecule in a first biological sample obtained from the individual immediately before administration of a first dose of an alpha-4 integrin inhibitor;

b) administering the first dose of the alpha-4 integrin inhibitor to the individual;

c) measuring the soluble molecule in a second biological sample, wherein the second biological sample is obtained from the individual within 1, 2, 3 4, 5, 6, 7, 8, 9, 10, 11, 12, 13, or 14 days after administration of the first dose of the alpha-4 integrin inhibitor;

d) determining whether there is a decrease in the levels of the soluble molecule between the first and the second biological samples; and e) administering a second dose of the alpha-4 integrin inhibitor to the individual, wherein the second dose of the alpha-4 integrin inhibitor is based on whether there is a decrease in the levels of the soluble molecule between the first and the second biological samples, wherein the decrease correlates with a decrease in alpha-4 integrin activity in the individual, and thereby determining whether there is a difference in alpha-4 integrin activity in the individual after administration of the alpha-4 integrin inhibitor compared with before administration of the alpha-4 integrin inhibitor;

wherein the soluble molecule is sVCAM and/or sMAdCAM, and wherein the alpha-4 integrin inhibitor is an anti-alpha-4 integrin antibody.

7. The method of claim 6, wherein the method comprises detecting no decrease or a statistically insignificant decrease ($p>0.05$) in the levels of sVCAM and/or sMAdCAM between the first and second biological samples, thereby determining that the first dose of the alpha-4 integrin inhibitor is ineffective and the method further comprises adjusting the second dose of the alpha-4 integrin inhibitor wherein the second dose is higher than the first dose.

8. The method of claim 6, wherein the method comprises detecting a statistically significant decrease ($p<0.05$) in the levels of sVCAM and/or sMAdCAM between the first and second biological samples, thereby determining that the first dose of the alpha-4 integrin inhibitor is effective and wherein the second dose is the same as the first dose.

9. The method of claim 6, wherein the autoimmune disease is selected from the group consisting of multiple sclerosis (MS), meningitis, encephalitis, inflammatory bowel disease, rheumatoid arthritis (RA), asthma, atherosclerosis, nephritis, atopic dermatitis, psoriasis, lupus erythematosus, and epilepsy.

10. The method of claim 6, wherein the soluble molecule is measured by a method selected from the group consisting of enzyme-linked immunosorbent assays (ELISA), radioimmunoassay (RIA), Western blotting, and microbead-based protein detection assay.

11. The method of claim 1, wherein the first biological sample and the second biological sample are each independently a bodily fluid selected from the group consisting of blood, serum, and plasma.

12. The method of claim 1, wherein the first and/or the second biological sample is in the form of frozen plasma or serum.

13. The method of claim 1, wherein the second biological sample is obtained from the individual one day after administration of the alpha-4 integrin inhibitor.

14. The method of claim 6, wherein the alpha-4 integrin activity is alpha-4 beta-1 integrin activity, and wherein the soluble molecule is sVCAM, and/or wherein alpha-4 integrin activity is alpha-4 beta-7 integrin activity, and wherein the soluble molecule is sMAdCAM.

15. The method of claim 6, wherein the alpha-4 integrin activity is alpha-4 beta-1 integrin activity, and wherein the soluble molecule is sVCAM.

16. The method of claim 6, wherein the first biological sample and the second biological sample are each independently a bodily fluid selected from the group consisting of blood, serum, and plasma.

17. The method of claim 6, wherein the first and/or the second biological sample is in the form of frozen plasma or serum.

18. The method of claim 6, wherein the second biological sample is obtained from the individual one day after administration of the alpha-4 integrin inhibitor.

* * * * *